US012728006B2

(12) United States Patent
Alghazali et al.

(10) Patent No.: US 12,728,006 B2
(45) Date of Patent: Sep. 8, 2026

(54) BIOCOMPATIBLE STRUCTURE, AND FABRICATING METHODS AND APPLICATIONS OF SAME

(71) Applicant: BOARD OF TRUSTEES OF THE UNIVERSITY OF ARKANSAS, Little Rock, AR (US)

(72) Inventors: Karrer M. Alghazali, Little Rock, AR (US); Viney Saini, Little Rock, AR (US); Zeid A. Nima, Little Rock, AR (US); Alexandru S. Biris, Little Rock, AR (US); Shawn E. Bourdo, Little Rock, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 1052 days.

(21) Appl. No.: 17/893,273

(22) Filed: Aug. 23, 2022

(65) Prior Publication Data

US 2022/0401218 A1 Dec. 22, 2022

Related U.S. Application Data

(63) Continuation-in-part of application No. 16/137,771, filed on Sep. 21, 2018, now abandoned, and a continuation-in-part of application No. 15/834,699, filed on Dec. 7, 2017, now abandoned, said application No. 16/137,771 is a continuation-in-part of application No. 15/834,699, filed on Dec. 7, 2017, now abandoned, which is a continuation-in-part of application No. 15/624,425, filed on Jun. 15, 2017, now Pat. No. 10,238,496.

(60) Provisional application No. 62/431,076, filed on Dec. 7, 2016.

(51) Int. Cl.
*A61F 2/28* (2006.01)
*A61L 27/56* (2006.01)
*A61F 2/30* (2006.01)

(52) U.S. Cl.
CPC ................ *A61F 2/28* (2013.01); *A61L 27/56* (2013.01); *A61F 2002/30062* (2013.01); *A61L 2430/02* (2013.01)

(58) Field of Classification Search
CPC .................................. A61F 2/28; A61L 27/56
See application file for complete search history.

(56) References Cited

U.S. PATENT DOCUMENTS

2007/0061015 A1* 3/2007 Jensen ................... A61L 27/58 623/23.76

* cited by examiner

*Primary Examiner* — Alma Pipic
(74) *Attorney, Agent, or Firm* — troutman pepper locke; Tim Tingkang Xia, Esq.

(57) ABSTRACT

A biocompatible structure includes a scaffold obtained from a 3D structure. The 3D structure includes base layered structures, each of which includes at least a first layer and a second layer surrounded by the first layer. The first layer includes at least one of first, second and third media. The second layer includes at least another of the first, second and third media. The first medium comprises bone particles. The second medium comprises a polymer dissolvable in a first solvent. The third medium comprises solid particulates dissolvable in a second solvent different than the first solvent. The 3D structure is treated with the second solvent to dissolve the solid particulates so as to form pores at positions of the solid particulates therein, thereby resulting in the scaffold having a porosity adjustable by sizes of the solid particulates and concentration of the solid particulates in the 3D structure.

19 Claims, 13 Drawing Sheets

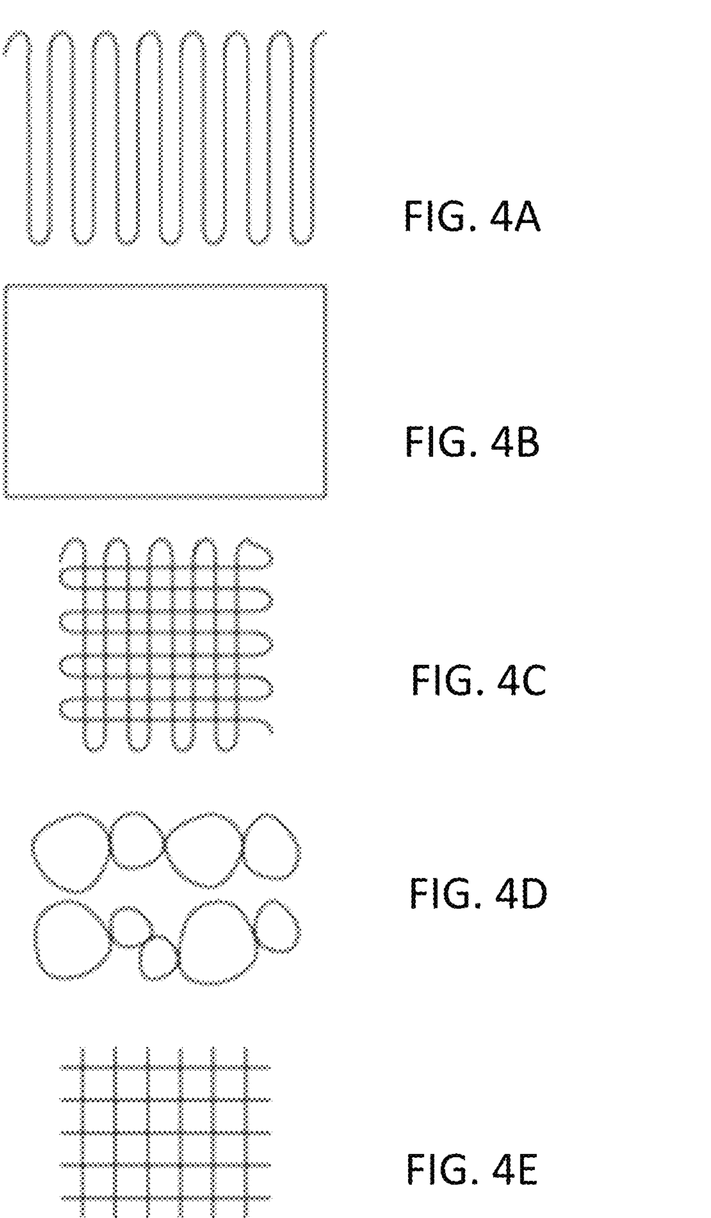
FIG. 4A
FIG. 4B
FIG. 4C
FIG. 4D
FIG. 4E
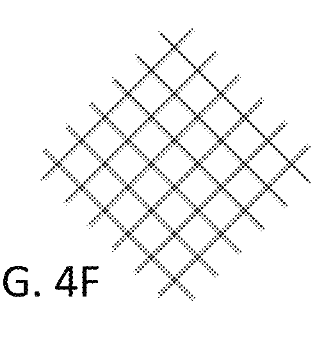
FIG. 4F
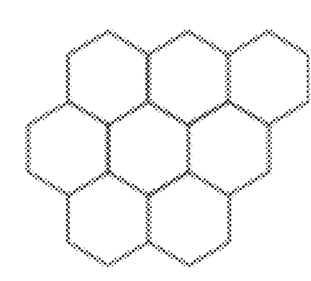
FIG. 4G 301/
301'
300
300
300
Medium 1
Medium 2
Medium 3/
Pores

302/
302'
301
301

303/
303'
301
301

304/
304'
301
301

Medium 3
520
Medium 1 +
Medium 2
510
522
512
300
501
Medium 1
Medium 2
Medium 3/
Pores
320
310
300/
300'

BIOCOMPATIBLE STRUCTURE, AND FABRICATING METHODS AND APPLICATIONS OF SAME

CROSS-REFERENCE TO RELATED PATENT APPLICATIONS

This application is a continuation-in-part of U.S. patent application Ser. No. 16/137,771, filed Sep. 21, 2018, which is a continuation-in-part of U.S. patent application Ser. No. 15/834,699, filed Dec. 7, 2017, which is a continuation-in-part of U.S. patent application Ser. No. 15/624,425, filed Jun. 15, 2017, now U.S. Pat. No. 10,238,496, and claims priority from U.S. provisional application Ser. No. 62/431,076, filed Dec. 7, 2016.

This application is also a continuation-in-part of U.S. patent application Ser. No. 15/834,699, filed Dec. 7, 2017, which is a continuation-in-part of U.S. patent application Ser. No. 15/624,425, filed Jun. 15, 2017, now U.S. Pat. No. 10,238,496, and claims priority from U.S. provisional application Ser. No. 62/431,076, filed Dec. 7, 2016.

Each of which is incorporated herein by reference in its entirety.

STATEMENT AS TO RIGHTS UNDER FEDERALLY-SPONSORED RESEARCH

This invention was made with government support under Contract No. W81XWH-15-1-0666 awarded by the Department of Defense (DOD-MRMCC). The government has certain rights in the invention.

FIELD

The present invention relates generally to a biocompatible structure having one or more base structures for bone and tissue regeneration, and more particularly to methods of fabricating tunable porous three-dimension (3D) biodegradable, biocompatible polymer/nanomaterial scaffolds and applications of the same.

BACKGROUND

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the present invention.

Regenerative medicine devices have proven to be valuable for tissue regenerations [5], where traditional clinical products such as autografts, allografts, and xenografts have a lot of obstacles that might cause failures [1]. The necessity to create alternative regeneration treatments to reach clinical trials has brought noticeable developments to artificial regenerative medicine device designs [3]. Although most of these developments are successful, they all have problems and limitations.

Therefore, a heretofore unaddressed need exists in the art to address the aforementioned deficiencies and inadequacies.

SUMMARY

One of the objectives of this invention is to provide a biocompatible structure having a scaffold that is a multistructural composite with tunable porosity for tissue regeneration as well as for delivery of bio-active molecules such as drugs, growth factors, and so on, and a fabricating method of the same.

In one aspect of the invention, the biocompatible structure useable for tissue regeneration, comprises a scaffold by treating a three-dimensional (3D) structure, the 3D structure comprising one or more base layered structures, wherein each base layered structure comprises at least a first layer and a second layer surrounded by the first layer, wherein the first layer and the second layer are formed of different materials, the first layer comprises at least one of a first medium, a second medium and a third medium, and the second layer comprises at least another of the first medium, the second medium and the third medium; wherein the first medium comprises bone particles, the second medium comprises a polymer that is dissolvable or removable in a first solvent, and the third medium comprises solid particulates alone or in polymeric structures that are dissolvable or removable in a second solvent different than the first solvent, wherein the 3D structure is treated with the second solvent to dissolve the solid particulates of the second medium therefrom so as to remove the solid particulates from the 3D structure and form pores at positions of the solid particulates therein, thereby resulting in the scaffold having a porosity that is adjustable by sizes of the solid particulates and concentration of the solid particulates in the 3D structure.

In one embodiment, the first layer comprises the first medium and the second medium, and the second layer comprises the third medium.

In one embodiment, the first layer comprises the first medium and the third medium, and the second layer comprises the second medium.

In one embodiment, the first layer comprises the second medium and the third medium, and the second layer comprises the first medium.

In one embodiment, the first layer comprises the first medium, and the second layer comprises the second medium and the third medium.

In one embodiment, the first layer comprises the second medium, and the second layer comprises the first medium and the third medium.

In one embodiment, the first layer comprises the second medium, and the second layer comprises the third medium.

In one embodiment, each base layered structure further comprises a third layer comprising the first medium deposited on the first layer.

In one embodiment, the 3D structure comprises a plurality of base layered structures attached to each other horizontally and/or vertically.

In one embodiment, the scaffold contains no polymer columns horizontally and/or vertically.

In one embodiment, the first medium and the second medium are arranged in layers with the second medium arranged in horizontal or vertical geometries.

In one embodiment, the first medium and the second medium arranged in alternating layers with the second medium arranged in horizontal and vertical geometries and the first medium disposed to separate the second medium horizontally and vertically.

In one embodiment, the second medium is deposited in a pattern including a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

In one embodiment, the bone particles comprise human bone particles, animal bone particles, and/or artificial bone particles.

In one embodiment, the bone particles have sizes in a range between 1 nm to 100 mm.

In one embodiment, the polymer is a natural or synthetic biocompatible and/or biodegradable polymer.

In one embodiment, the third medium comprises solid particulates that dissolve when immersed in liquid or gaseous solvent environments or based on temperature differentials and that do not immediately interact with the first medium and the second medium.

In one embodiment, the third medium is a single or a mixture of rapidly dissolving polymers in a solvent that immediately interacts with the first medium and the second medium.

In one embodiment, the third medium is a single rapidly dissolving polymer or a mixture of rapidly dissolving polymers in a solvent that does not immediately interact with the first medium and the second medium.

In one embodiment, the 3D structure further comprises at least a fourth medium, and wherein the at least fourth medium material is a polymer with a faster or longer bio-degradation time in a biological system compared to the second medium.

In one embodiment, the at least fourth medium materials are loaded with a variety of solid particulates similar to the second medium or the third medium in weight ratios varying from 0.01 to 99.99 wt. %.

In one embodiment, each of the second medium, the third medium and the at least fourth medium has degradation rates ranging from 1 second to 100 months.

In one embodiment, the at least fourth medium is independent or along with the second medium and is deposited in equal or variable ratios compared to the second medium.

In one embodiment, the at least one fourth medium is deposited in equal or variable ratios compared to the second medium.

In one embodiment, the second medium, the third medium and the at least fourth medium are deposited by a variety of methods that comprises electro-spraying, air deposition, bio-printing, extrusion, poring and curtain polymer deposition.

In one embodiment, the porosity of the scaffold is controlled by the deposition parameters, density of component materials and packing; and the porosity of the scaffold varies from 1 to 99%. In one embodiment, the size of the pores is between 0.1 nm to 3 mm. In another embodiment, the size of the pores is between 0.1 nm to 50 μm. In yet another embodiment, the size of the pores is between 0.1 nm to 1 μm.

In one embodiment, the scaffold is loaded with a plurality of cells, a plurality of drugs, or a plurality of growth factors.

In one embodiment, the scaffold is exposed to a gas plasma or corona discharge process in order to induce surface charges of positive, neutral, or negative polarity so as to increase the roughness of the surface morphology and introduce atoms and functional groups onto the surface.

In one embodiment, the scaffold is designed to have a non-uniform density and packing density.

In one embodiment, construction of the scaffold is done by using 3D bio-printing and hybrid printing technology by layer-by-layer deposition.

In one embodiment, the 3D structure is formed from successive layers to be mechanically modeled into a plurality of shapes and the successive layers are applied with mechanical pressure for compaction, shaping or modelling.

In one embodiment, the 3D structure is formed by a multi-nozzle deposition system having multiple nozzles controlled individually.

In one embodiment, the multi-nozzle deposition system comprises dual nozzles having an outer extruder nozzle and an inner extruder nozzle being inside of the outer extruder nozzle concentrically or eccentrically, wherein the first layer is formed with the outer extruder nozzle and the second layer is formed with the inner extruder nozzle.

In one embodiment, construction of the scaffold is done by using 3D bio-printing and hybrid printing technology by layer-by-layer deposition.

In one embodiment, the 3D structure is formed from successive layers to be mechanically modeled into various shapes and the successive layers are applied with mechanical pressure for compaction, shaping or modelling.

In another aspect of the invention, the method for fabricating a scaffold useable for tissue regeneration comprises providing a plurality of materials comprising a first medium, a second medium and a third medium, wherein the first medium comprises bone particles, the second medium comprises a polymer that is dissolvable or removable in a first solvent, and the third medium comprises solid particulates alone or in polymeric structures that are dissolvable or removable in a second solvent different than the first solvent; forming a 3D structure comprising one or more base layered structures, wherein each base layered structure comprises at least a first layer and a second layer surrounded by the first layer, wherein the first layer and the second layer are formed of different materials, the first layer comprises at least one of the first, second and third media, and the second layer comprises at least another of the first, second and third media; and treating the 3D structure with the second solvent to dissolve the solid particulates of the second medium therefrom so as to remove the solid particulates from the 3D structure and form pores at positions of the solid particulates therein, thereby forming the scaffold having a porosity that is adjustable by sizes of the solid particulates and concentration of the solid particulates in the 3D structure.

In one embodiment, the first layer comprises the first medium and the second medium, and the second layer comprises the third medium.

In one embodiment, the first layer comprises the first medium and the third medium, and the second layer comprises the second medium.

In one embodiment, the first layer comprises the second medium and the third medium, and the second layer comprises the first medium.

In one embodiment, the first layer comprises the first medium, and the second layer comprises the second medium and the third medium.

In one embodiment, the first layer comprises the second medium, and the second layer comprises the first medium and the third medium.

In one embodiment, the first layer comprises the second medium, and the second layer comprises the third medium.

In one embodiment, each base layered structure further comprises a third layer comprising the first medium deposited on the first layer.

In one embodiment, the 3D structure comprises a plurality of base layered structures attached to each other horizontally and/or vertically.

In one embodiment, the 3D structure contains no polymer columns horizontally and/or vertically.

In one embodiment, said forming the 3D structure is performed by a multi-nozzle deposition system having multiple nozzles controlled individually.

In one embodiment, the multi-nozzle deposition system comprises dual nozzles having an outer extruder nozzle and an inner extruder nozzle being inside of the outer extruder nozzle concentrically or eccentrically, wherein the first layer is formed with the outer extruder nozzle and the second layer is formed with the inner extruder nozzle.

In one embodiment, the 3D structure is formed from successive layers to be mechanically modeled into various shapes and the successive layers are applied with mechanical pressure for compaction, shaping or modelling.

In one embodiment, the first medium is deposited by a powder dispersion technique that comprises uses of shaking, controlled deposition, electrostatic deposition, dry powder deposition, powder deposition in a liquid that is a solvent of one of the first medium, the second medium, the third medium and the at least fourth medium, laser deposition, powder jet deposition, and electrospray.

In one embodiment, the second medium, the third medium and the at least fourth medium are deposited by a variety of methods that comprises electro-spraying, air deposition, bio-printing, extrusion, poring and curtain polymer deposition.

In one embodiment, the porosity of the scaffold is controlled by the deposition parameters, density of component materials and packing; the pores is between 0.1 nm to 3 mm, and the porosity of the scaffold varies from 1 to 99%.

In one embodiment, the scaffold is loaded with a plurality of cells, a plurality of drugs, or a plurality of growth factors.

In one embodiment, the scaffold is exposed to a gas plasma or corona discharge process in order to induce surface charges of positive, neutral, or negative polarity so as to increase the roughness of the surface morphology and introduce atoms and functional groups onto the surface.

In one embodiment, the scaffold is designed to have a non-uniform density and packing density.

In one embodiment, construction of the scaffold is done by using 3D bio-printing and hybrid printing technology by layer-by-layer deposition.

In one embodiment, the bone particles comprise human bone particles, animal bone particles, and/or artificial bone particles.

In one embodiment, the bone particles have sizes in a range between 1 nm to 100 mm. In one embodiment, the polymer is a natural or synthetic biocompatible and/or biodegradable polymer.

In one embodiment, the first medium and the second medium are arranged in layers with the second medium arranged in horizontal or vertical geometries.

In one embodiment, the second medium is deposited in a pattern including a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

In one embodiment, the third medium comprises solid particulates that dissolve when immersed in liquid or gaseous solvent environments or based on temperature differentials and that do not immediately interact with the first medium and the second medium.

In one embodiment, the third medium is a single or a mixture of rapidly dissolving polymers in a solvent that immediately interacts with the first medium and the second medium.

In one embodiment, the third medium is a single rapidly dissolving polymer or a mixture of rapidly dissolving polymers in a solvent that does not immediately interact with the first medium and the second medium.

In one embodiment, the plurality of materials further comprise at least a fourth medium, and wherein the at least fourth medium material is a polymer with a faster or longer bio-degradation time in a biological system compared to the second medium.

In one embodiment, the at least fourth medium materials are loaded with a variety of solid particulates similar to the second medium or the third medium in weight ratios varying from 0.01 to 99.99 wt. %.

In one embodiment, each of the second medium, the third medium and the at least fourth medium has degradation rates ranging from 1 second to 100 months.

In one embodiment, the at least fourth medium is independent or along with the second medium and is deposited in equal or variable ratios compared to the second medium.

These and other aspects of the invention will become apparent from the following description of the preferred embodiment taken in conjunction with the following drawings, although variations and modifications therein may be affected without departing from the spirit and scope of the novel concepts of the invention.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 4A-4G show schematically patterns of deposition of various media according to certain embodiments of the invention.

DETAILED DESCRIPTION

Figure 1A:
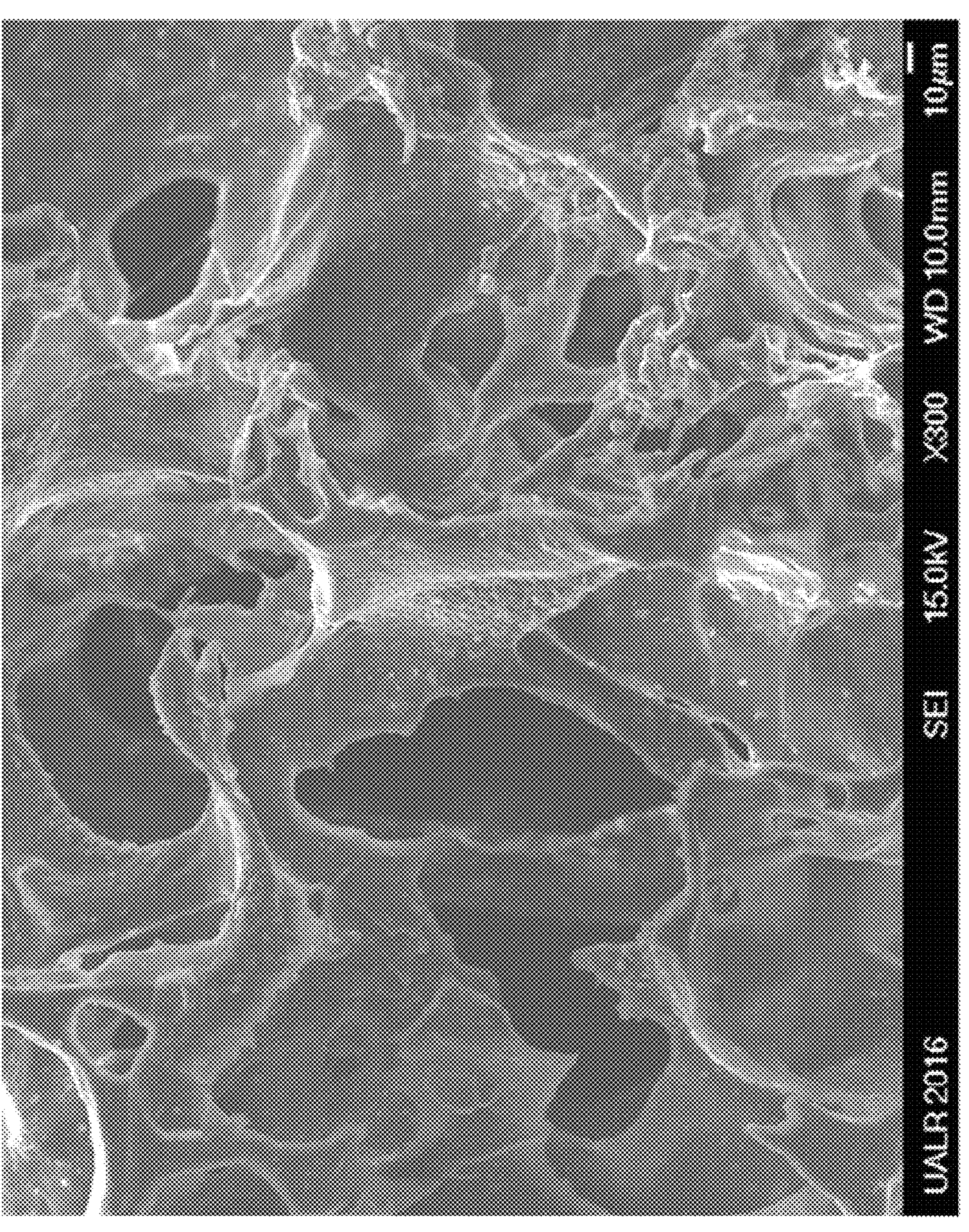
FIGS. 1A-1D show SEM images of a biocompatible structure in different spots according to certain embodiments of the invention. The SEM images show the scaffold having a 3D structure having a tunable porosity with interconnected channels and pores along with adjustable dimensions.
Figure 1B:
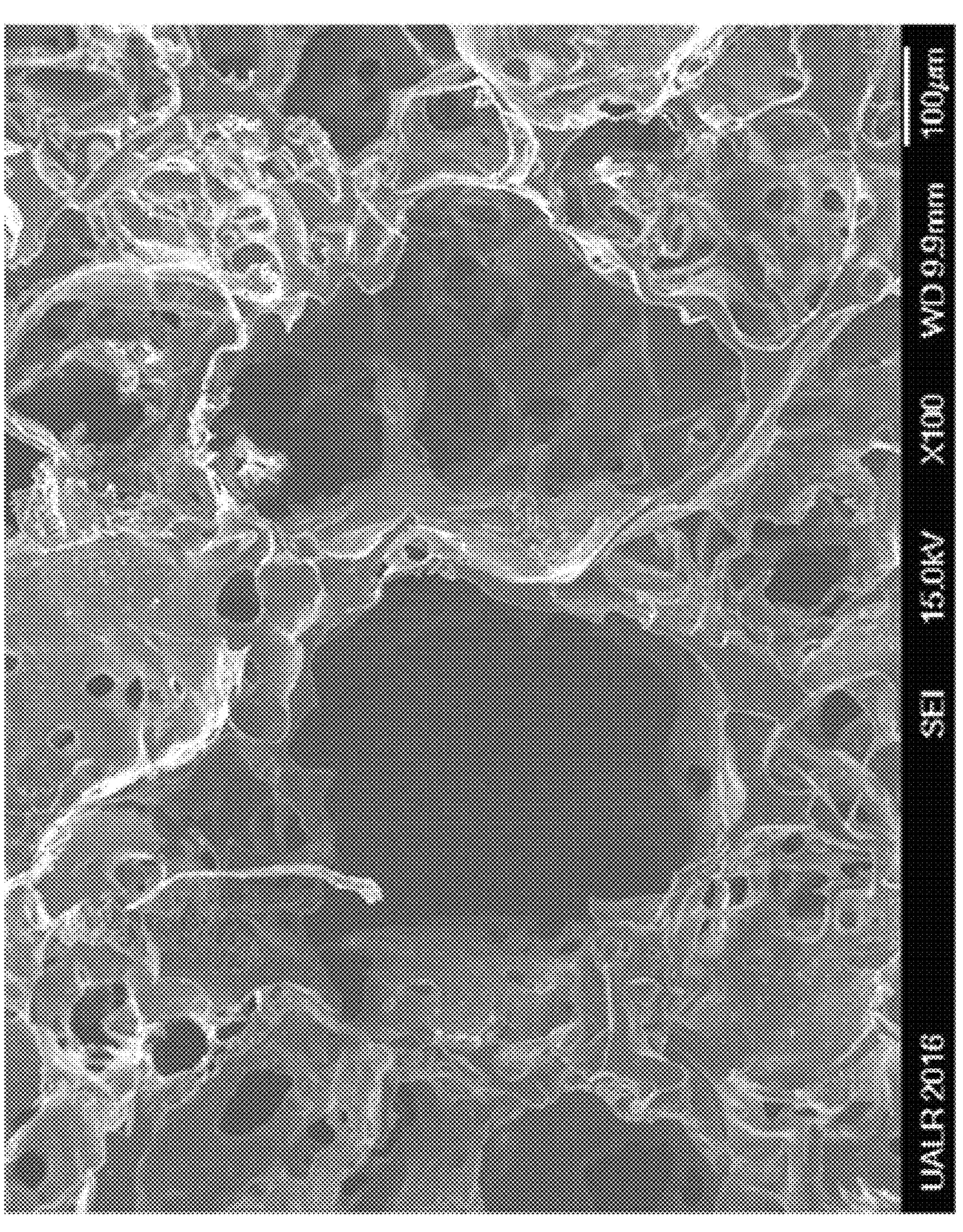
Figure 1C:
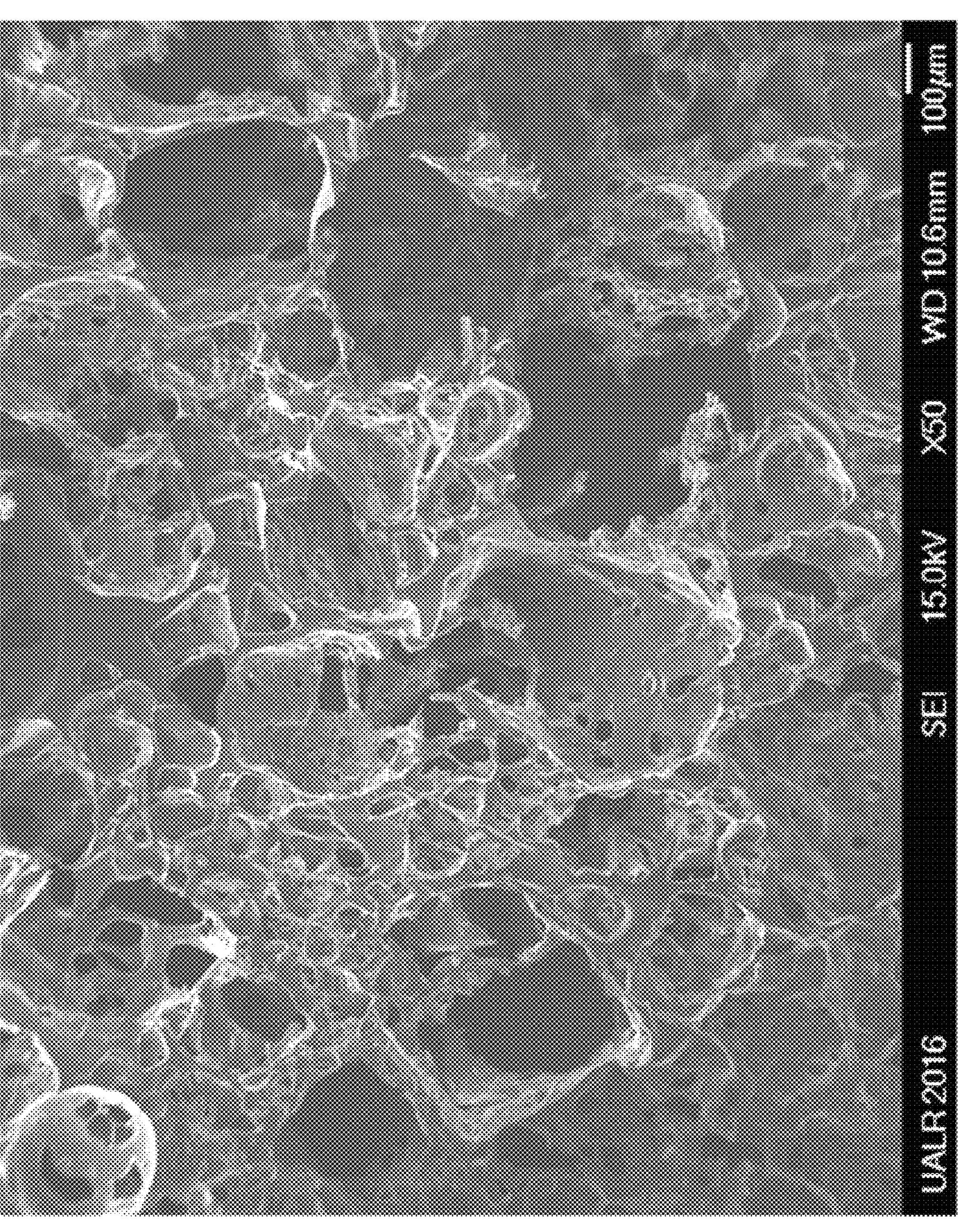
Figure 1D:
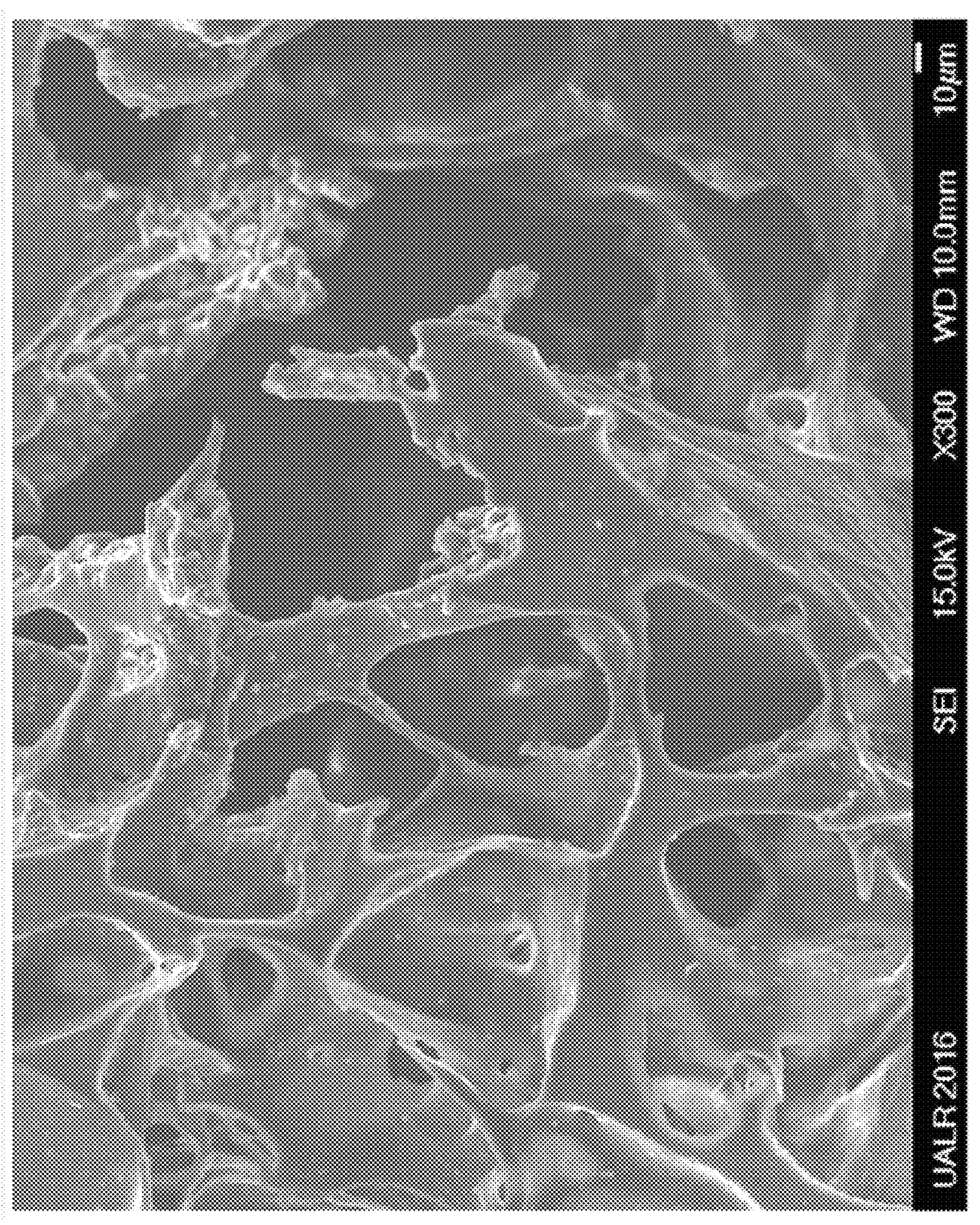

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting and/or capital letters has no influence on the scope and meaning of a term; the scope and meaning of a term are the same, in the same context, whether or not it is highlighted and/or in capital letters. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the invention.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, the terms “comprise” or “comprising”, “include” or “including”, “carry” or “carrying”, “has/have” or “having”, “contain” or “containing”, “involve” or “involving” and the like are to be understood to be open-ended, i.e., to mean including but not limited to.

As used herein, the phrase “at least one of A, B, and C” should be construed to mean a logical (A or B or C), using a non-exclusive logical OR. It should be understood that one or more steps within a method may be executed in different order (or concurrently) without altering the principles of the invention.

As used herein, terms such as “about”, “approximately”, “generally”, “substantially”, and the like unless otherwise indicated mean within 20 percent, preferably within 10 percent, preferably within 5 percent, and even more preferably within 3 percent of a given value or range. Numerical quantities given herein are approximate, meaning that the term “about”, “approximately”, “generally”, or “substantially” can be inferred if not expressly stated.

As used herein, the terms, “nanoscopic-scale”, “nanoscopic”, “nanometer-scale”, “nanoscale”, the “nano-” prefix, and the like refers to elements or articles having widths or diameters of less than about 1 μm, preferably less than about 100 nm in some cases. Specified widths can be smallest width (i.e. a width as specified where, at that location, the article can have a larger width in a different dimension), or largest width (i.e., where, at that location, the article's width is no wider than as specified, but can have a length that is greater), unless pointed out otherwise.

As used herein, the term “porosity” refers to the ratio of volume of pores to its total volume of a scaffold.

Embodiments of the invention are illustrated in detail hereinafter with reference to accompanying drawings. It should be understood that specific embodiments described herein are merely intended to explain the invention, but not intended to limit the invention. In accordance with the purposes of this invention, as embodied and broadly described herein, this invention, in certain aspects, relates to tunable porous three-dimension (3D) biodegradable, biocompatible polymer/nanomaterial biocompatible structures and fabricating methods and applications of the same.

In most of the tissue trauma, there is loss of more than one type of tissues in an implant surgical site of a human or an animal. A biocompatible structure can be adapted to include multiple base structures having different properties, thus facilitating regeneration of two or more tissues in the implant surgical site of the human or the animal, or facilitating regeneration of tissues in a non-implant surgical site of the human or the animal and then transferred to the implant site, or facilitating regeneration of tissues in vitro or in the lab and then transferred to the implant surgical site. Alternatively, the biocompatible structure can have only one base structure.

In certain aspects, the invention provides a biocompatible structure having a scaffold that is a multistructural composite with tunable characteristics for tissue regeneration as well as for delivery of bio-active molecules such as drugs, growth factors, and so on, and a fabricating method of the same.

In some embodiments, the scaffold has a tunable porosity with interconnected channels and pores along with adjustable dimensions. The scaffold is obtained from a 3D structure formed of at least one of medium A, medium B, medium C and medium D. In some embodiments, by removing medium B from the 3D structure, the scaffold is formed to have pores at positions of medium B.

In some embodiments, medium A includes one or more polymers that are biocompatible and biodegradable. In some embodiments, the one or more polymers include one or more of polyurethanes, polyether urethanes, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosinetyrosylhexyl ester iminocarbonate) (poly(DTH iminocarbonate)), poly(bisphenol A iminocarbonate), poly(ortho ester), polycyanoacrylate, polyphosphazene, poly(α-esters), poly(L-lactic acid) (PLLA), poly(D-lactic acid) (PDLA), poly(D, L-lactic acid) (PDLLA), polyhydroxyalkanoates, poly(3-hydroxybutyrate-co-3-hydroxyvalerate) (PHBV), poly(propylene fumarate) (PPF), polyacetals, poly(ortho esters), polycarbonates, poly(desaminotyrosyltyrosine alkyl ester carbonates) (PDTEs), polyurethanes, poly[bis(trifluoroethoxy) phosphazene], polyphosphoesters, polyesters, polyethers, poly(β-amino esters) (PBAEs), poly(anhydride ester)s, poly (ester urethane), poly(ethylene glycol) (PEG), poly(propylene glycol) (PPG), pluronic P-123 including poly(ethylene glycol)-block-poly(propylene glycol)-block-poly(ethylene glycol) (PEG-PPG-PEG), PEG diacrylate (PEGDA), PEG dimethacrylate (PEGDMA), elastin and elastin-like polypeptides (ELPs), albumin, poly(amino acids), poly(γ-glutamic acid), poly(L-lysine), poly(L-glutamic acid), poly(aspartic acid), poly(aspartic acid) (PAA), hyaluronic acid (HA), chondroitin sulfate (CS), chitosan, alginate, agarose, mannan, and/or inulin, or a polymer derived from natural source including polysaccharides, proteins, or a mixture thereof.

In some embodiments, medium A is combinable with ethanol, methanol, or other organic solvents or mixtures thereof.

In some embodiments, medium B includes one or more soluble materials, and is mixable with medium A. In some embodiments, the one or more soluble materials have a rate of degradation or dissolution that is faster than that of medium A in a solvent, and include soluble crystals including sodium, chloride, sugar, or other material.

In some embodiments, medium C includes fillers of one or more insoluble materials having structures with dimensions between 1 nm to 5 mm, and is mixable in a bulk or surface of medium A or medium B individually, or in a bulk or surface of a combination of medium A and medium B. In some embodiments, the one or more insoluble materials include at least one of metal materials including gold, silver, copper, or other metals, or a combination of them, with micro-sized and/or nano-sized structures of various shapes including spheres, rods, platelets, cylinders, cubes, pyramids, cavities, nanoshells, nanocages, or the likes; carbonaceous materials including nanotubes, graphene, nanofibers, nanoonions, nanocones, or the likes; micro-sized or nano-sized hydroxyapatite; bone component particles, and/or bone component nanoparticles; calcium phosphate; and micro-sized and/or micro-sized ceramics.

In some embodiments, medium D includes an agent. In some embodiments, the agent includes deionized (DI) water, sodium hydroxide, ethanol, methanol, or other organic solvents, or mixtures thereof.

In some embodiments, a mixture of media A-C is obtained in bulks, layers, or concentrically arranged geometries by using at least one process of mixing, spraying, electrospraying, extrusion, layer-by-layer deposition, and the likes.

In some embodiments, the mixture of the media A-C is operably exposed to medium D to remove medium B without adversely affecting medium A or medium C, so as to form a first composite.

In some embodiments, medium D is operably removed from the first composite by at least one process of evaporating, drying, heating, vacuum drying, freeze-drying, and the likes, so as to form a second composite.

In some embodiments, the second composite is operably exposed to a plasma treatment for the surface modification to alter its surface chemistry. The plasma treatment is performed in at least one gas of oxygen, nitrogen, helium, argon, and the likes.

In some embodiments, a concentration ratio of medium C to medium A is in a range of 0.01-99.99 in the second composite.

In some embodiments, the scaffold has a shape and size conforming to a shape and size of corresponding tissue that needs to be regenerated.

In some embodiments, the scaffold is capable of incubating or incorporating various types of nanoparticles, cells, bioactive materials, growth factors, and/or tissue regeneration enhancing drugs therein.

In some embodiments, internal and external surfaces of the scaffold and/or a bulk of the scaffold are coated with nanostructural materials.

In some embodiments, the tunable porosity of the scaffold is tunable with pore sizes from 0.1 nm to 10 mm, and the surface area of the scaffold is between 0.001 and 5000 $m^2/g$.

As formed, the artificial regenerative medicine scaffold is biocompatible, biodegradable and able to form any shape necessary based on the wound. The scaffold has a tunable porosity with interconnection channels, which is sufficient to allow cell migration, diffusion of the nutrition and bodily fluids [2, 4]. The scaffold incorporates within its structure or on its surface tissue regeneration enhancement additives, which are one or more of, but are not limited to:

- cells, including, but are not limited to, epithelial cells, neurons, glial cells, astrocytes, podocytes, mammary epithelial cells, islet cells, endothelial cells, mesenchymal cells, stem cells, osteoblast, muscle cells, striated muscle cells, fibroblasts, hepatocytes, ligament fibroblasts, tendon fibroblasts, chondrocytes, or a mixture thereof;
- bioactive materials, including, but are not limited to, proteins, enzymes, growth factors, amino acids, bone morphogenic proteins, platelet derived growth factors, vascular endothelial growth factors, or a mixture thereof;
- drugs, antimicrobials, anti-inflammatory [6];
- particles and nanoparticles, including, but are not limited to, gold, silver, copper, nanoparticles, nanorods, nanocubes, nanoplates, nanocavities, nanostars, nanopyramids, graphene, nanohydroxyapatite, hydroxyapatite, calcium phosphate, bone particles and nanoparticles, ceramic particles and nanoparticles, and so on; and
- polymers and nanostructures and nano-sized polymers, biocompatible and biodegradable polymers, natural and synthetic polymers and hydrogels.

In addition, the scaffold fits with different kinds of tissue regeneration such as nerve, bone, cartilage, arteries, skin, or any other type of hard/soft tissues where a scaffold is required for the regenerative processes. In certain embodiments, a tunable porosity with interconnected channels and pores along with adjustable dimensions for the scaffold is shown in FIGS. 1A-1D. In certain embodiments, the tunable porosity can be achieved through 3D printing. In addition, the ability to incubate or incorporate within the scaffold with various types of nanoparticles, stem cells, tissue regeneration enhancing drugs is also unique. Furthermore, the scaffold composite can be arranged in layers with various materials in between.

In one aspect, the invention relates to a method for fabricating a scaffold useable for tissue regeneration. In some embodiments, the method includes providing medium A, medium B, medium C and medium D.

Medium A includes one or more polymers that are biocompatible and biodegradable. In some embodiments, the one or more polymers include polyurethanes, polylactide (PLA), polyglycolide (PGA), poly(lactide-co-glycolide) (PLGA), poly(e-caprolactone), polydioxanone, polyanhydride, trimethylene carbonate, poly(β-hydroxybutyrate), poly(g-ethyl glutamate), poly(desaminotyrosinetyrosylhexyl ester iminocarbonate) (poly(DTH iminocarbonate), poly(bisphenol A iminocarbonate), poly(ortho ester), polycyanoacrylate, polyphosphazene, a polymer derived from natural source including polysaccharides, proteins, or a mixture thereof. In some embodiments, medium A is combinable with ethanol, methanol, or other organic solvents or mixtures thereof.

Medium B includes one or more soluble materials, and is mixable with medium A. In some embodiments, the one or more soluble materials have a rate of degradation or dissolution that is faster than that of medium A in a solvent, and include soluble crystals including sodium, chloride, sugar, or other material.

Medium C includes fillers of one or more insoluble materials having structures with dimensions between 1 nm to 5 mm, and is mixable in a bulk or surface of medium A or medium B individually, or in a bulk or surface of a combination of medium A and medium B. In some embodiments, the one or more insoluble materials include at least one of metal materials including gold, silver, copper, or other metals, or a combination of them, with micro-sized and/or nano-sized structures of various shapes including spheres, rods, platelets, cylinders, cubes, pyramids, cavities, nanoshells, nanocages, or the likes; carbonaceous materials including nanotubes, graphene, nanofibers, nanoonions, nanocones, or the likes; micro-sized or nano-sized hydroxyapatite; bone component particles, and/or bone component nanoparticles; calcium phosphate; and micro-sized and/or micro-sized ceramics.

Medium D includes an agent. In some embodiments, the agent includes deionized (DI) water, sodium hydroxide, ethanol, methanol, or other organic solvents, or mixtures thereof.

In addition, the method also includes forming a mixture of media A-C in bulks, layers, or concentrically arranged geometries by at least one process of mixing, spraying, electrospraying, extrusion, layer-by-layer deposition, and the likes; exposing the mixture of media A-C to medium D to remove medium B without adversely affecting medium A and medium C, so as to form a first composite; and removing medium D from the first composite by at least one process of evaporating, drying, heating, vacuum drying, freeze-drying, and the likes, so as to form the scaffold. As formed, the scaffold has a tunable porosity with interconnected channels and pores along with adjustable dimensions.

In some embodiments, the method further includes performing a plasma treatment to the scaffold for the surface modification to alter its surface chemistry. The plasma treatment is performed in at least one gas of oxygen, nitrogen, helium, argon, and the likes.

In some embodiments, the scaffold is capable of incubating or incorporating various types of nanoparticles, cells, bioactive materials, growth factors, and/or tissue regeneration enhancing drugs therein.

In some embodiments, internal and external surfaces of the scaffold and/or a bulk of the 3D structure are coated with nanostructural materials.

In some embodiments, the scaffold has a shape and size conforming to a shape and size of corresponding tissue that needs to be regenerated.

In some embodiments, a concentration ratio of medium C to medium A is in a range of 0.01-99.99 in the scaffold.

In some embodiments, the tunable porosity of the scaffold is tunable with pore sizes from 0.1 nm to 10 mm. In one embodiment, the size of the pores is between 0.1 nm to 3 mm. In other embodiments, the size of the pores can be between 0.1 nm to 1 mm, between 0.1 nm to 500 μm, between 0.1 nm to 200 μm, between 0.1 nm to 100 μm, between 0.1 nm to 50 μm, between 0.1 nm to 10 between 0.1 nm to 5 or between 0.1 nm to 1 μm. In some embodiments, the surface area of the scaffold is between 0.001 and 5000 $m^2/g$. Preferably, the surface area of the scaffold is between 0.001 and 50 $m^2/g$, between 50 and 100 $m^2/g$, between 100 and 120 $m^2/g$, between 120 and 150 $m^2/g$, between 150 and 200 $m^2/g$, between 200 and 500 $m^2/g$, between 500 and 1000 $m^2/g$, or between 1000 and 5000 $m^2/g$.

In some embodiments, the tunable porosity is achievable through 3D printing.

In another aspect, the invention relates to a method for fabricating a scaffold useable for tissue regeneration. In some embodiments, the method includes providing medium A, medium B, medium C and medium D, as disclosed above.

The method also includes mixing medium B with medium A until a paste-like state is achieved, to form a mixture. The mixing ratio between the biodegradable polymer and the soluble crystals can be altered depend on the quantity of the porosity within the scaffold, In one mixture, around 90% porosity were achieved within the structure.

The method also includes exposing the mixture to medium D to solidify the one or more polymers so as to form the scaffold; transferring the scaffold in a water bath that is placed on an orbital shaker and leaching the one or more soluble materials from the scaffold with DI water; and drying and sterilizing the scaffold.

In some embodiments, the mixing step includes adding nanoparticles microparticles, growth factors, and/or tissue regeneration enhancing drugs when mixing medium A and medium B to form the mixture, so that the nanoparticles microparticles, and/or tissue regeneration enhancing drugs are incubated and incorporated within the scaffold.

In some embodiments, the method further includes immersing the sterilized scaffold the inside the solution contain nanoparticles microparticles, growth factors, and/or tissue regeneration enhancing drugs for a predetermined period.

In some embodiments, the exposing step includes placing the mixture in a syringe having desired size and diameter; and extruding the mixture by the syringe inside a container contains medium E, so that the scaffold has a shape and size conforming to a shape and size of corresponding tissue that needs to be regenerated.

In certain aspects, the invention relates to methods for fabrication of multistructural composite materials that support tissue regeneration or act as delivery devices for bioactive molecules. The multistructural composite has a tunable porosity, tunable mechanical properties, and architecture, and is defined such that it can support cellular proliferation, deliver various drugs of growth factors. The technology has the following functions: tissue regeneration, support cellular proliferation, deliver bio-active molecules.

In one aspect, the invention relates to a biocompatible structure useable for tissue regeneration comprising a scaffold by treating a 3D structure, the 3D structure comprising one or more base layered structures, wherein each base layered structure comprises at least a first layer and a second layer surrounded by the first layer, wherein the first layer and the second layer are formed of different materials, the first layer comprises at least one of a first medium, a second medium and a third medium, and the second layer comprises at least another of the first medium, the second medium and the third medium; wherein the first medium comprises bone particles, the second medium comprises a polymer that is dissolvable or removable in a first solvent, and the third medium comprises solid particulates alone or in polymeric structures that are dissolvable or removable in a second solvent different than the first solvent, wherein the 3D structure is treated with the second solvent to dissolve the solid particulates of the second medium therefrom so as to remove the solid particulates from the 3D structure and form pores at positions of the solid particulates therein, thereby resulting in the scaffold having a porosity that is adjustable by sizes of the solid particulates and concentration of the solid particulates in the 3D structure.

In some embodiments, the first layer comprises the first medium and the second medium, and the second layer comprises the third medium.

In some embodiments, the first layer comprises the first medium and the third medium, and the second layer comprises the second medium.

In some embodiments, the first layer comprises the second medium and the third medium, and the second layer comprises the first medium.

In some embodiments, the first layer comprises the first medium, and the second layer comprises the second medium and the third medium.

In some embodiments, the first layer comprises the second medium, and the second layer comprises the first medium and the third medium.

In some embodiments, the first layer comprises the second medium, and the second layer comprises the third medium.

In some embodiments, each base layered structure further comprises a third layer comprising the first medium deposited on the first layer.

In some embodiments, the 3D structure comprises a plurality of base layered structures attached to each other horizontally and/or vertically.

In some embodiments, the scaffold contains no polymer columns horizontally and/or vertically.

In some embodiments, the first medium and the second medium are arranged in layers with the second medium arranged in horizontal or vertical geometries.

In some embodiments, the first medium and the second medium arranged in alternating layers with the second medium arranged in horizontal and vertical geometries and the first medium disposed to separate the second medium horizontally and vertically.

In some embodiments, the second medium is deposited in a pattern including a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

In some embodiments, the bone particles comprise human bone particles, animal bone particles, and/or artificial bone particles.

In some embodiments, the bone particles have sizes in a range between 1 nm to 100 mm.

In some embodiments, the polymer is a natural or synthetic biocompatible and/or biodegradable polymer.

In some embodiments, the third medium comprises solid particulates that dissolve when immersed in liquid or gaseous solvent environments or based on temperature differentials and that do not immediately interact with the first medium and the second medium.

In some embodiments, the third medium is a single or a mixture of rapidly dissolving polymers in a solvent that immediately interacts with the first medium and the second medium.

In some embodiments, the third medium is a single rapidly dissolving polymer or a mixture of rapidly dissolving polymers in a solvent that does not immediately interact with the first medium and the second medium.

In some embodiments, the 3D structure further comprises at least a fourth medium, and wherein the at least fourth medium material is a polymer with a faster or longer bio-degradation time in a biological system compared to the second medium.

In some embodiments, the at least fourth medium materials are loaded with a variety of solid particulates similar to the second medium or the third medium in weight ratios varying from 0.01 to 99.99 wt. %.

In some embodiments, each of the second medium, the third medium and the at least fourth medium has degradation rates ranging from 1 second to 100 months.

In some embodiments, the at least fourth medium is independent or along with the second medium and is deposited in equal or variable ratios compared to the second medium.

In some embodiments, the at least one fourth medium is deposited in equal or variable ratios compared to the second medium.

In some embodiments, the second medium, the third medium and the at least fourth medium are deposited by a variety of methods that comprises electro-spraying, air deposition, bio-printing, extrusion, poring and curtain polymer deposition.

In some embodiments, the porosity of the scaffold is controlled by the deposition parameters, density of component materials and packing; the pores is between 0.1 nm to 3 mm, and the porosity of the scaffold varies from 1 to 99%.

In some embodiments, the scaffold is loaded with a plurality of cells, a plurality of drugs, or a plurality of growth factors.

In some embodiments, the scaffold is exposed to a gas plasma or corona discharge process in order to induce surface charges of positive, neutral, or negative polarity so as to increase the roughness of the surface morphology and introduce atoms and functional groups onto the surface.

In some embodiments, the scaffold is designed to have a non-uniform density and packing density.

In some embodiments, construction of the scaffold is done by using 3D bio-printing and hybrid printing technology by layer-by-layer deposition.

In some embodiments, the 3D structure is formed from successive layers to be mechanically modeled into a plurality of shapes and the successive layers are applied with mechanical pressure for compaction, shaping or modelling.

In some embodiments, the 3D structure is formed by a multi-nozzle deposition system having multiple nozzles controlled individually.

In some embodiments, the multi-nozzle deposition system comprises dual nozzles having an outer extruder nozzle and an inner extruder nozzle being inside of the outer extruder nozzle concentrically or eccentrically, wherein the first layer is formed with the outer extruder nozzle and the second layer is formed with the inner extruder nozzle.

In some embodiments, construction of the scaffold is done by using 3D bio-printing and hybrid printing technology by layer-by-layer deposition.

In some embodiments, the 3D structure is formed from successive layers to be mechanically modeled into various shapes and the successive layers are applied with mechanical pressure for compaction, shaping or modelling.

In another aspect, the invention relates to a method for fabricating a scaffold useable for tissue regeneration comprising providing a plurality of materials comprising a first medium, a second medium and a third medium, wherein the first medium comprises bone particles, the second medium comprises a polymer that is dissolvable or removable in a first solvent, and the third medium comprises solid particulates alone or in polymeric structures that are dissolvable or removable in a second solvent different than the first solvent; forming a 3D structure comprising one or more base layered structures, wherein each base layered structure comprises at least a first layer and a second layer surrounded by the first layer, wherein the first layer and the second layer are formed of different materials, the first layer comprises at least one of the first, second and third media, and the second layer comprises at least another of the first, second and third media; and treating the 3D structure with the second solvent to dissolve the solid particulates of the second medium therefrom so as to remove the solid particulates from the 3D structure and form pores at positions of the solid particulates therein, thereby forming the scaffold having a porosity that is adjustable by sizes of the solid particulates and concentration of the solid particulates in the 3D structure.

In some embodiments, the first layer comprises the first medium and the second medium, and the second layer comprises the third medium.

In some embodiments, the first layer comprises the first medium and the third medium, and the second layer comprises the second medium.

In some embodiments, the first layer comprises the second medium and the third medium, and the second layer comprises the first medium.

In some embodiments, the first layer comprises the first medium, and the second layer comprises the second medium and the third medium.

In some embodiments, the first layer comprises the second medium, and the second layer comprises the first medium and the third medium.

In some embodiments, the first layer comprises the second medium, and the second layer comprises the third medium.

In some embodiments, each base layered structure further comprises a third layer comprising the first medium deposited on the first layer.

In some embodiments, the 3D structure comprises a plurality of base layered structures attached to each other horizontally and/or vertically.

In some embodiments, the 3D structure contains no polymer columns horizontally and/or vertically.

In some embodiments, said forming the 3D structure is performed by a multi-nozzle deposition system having multiple nozzles controlled individually.

In some embodiments, the multi-nozzle deposition system comprises dual nozzles having an outer extruder nozzle and an inner extruder nozzle being inside of the outer extruder nozzle concentrically or eccentrically, wherein the first layer is formed with the outer extruder nozzle and the second layer is formed with the inner extruder nozzle.

In some embodiments, the 3D structure is formed from successive layers to be mechanically modeled into various shapes and the successive layers are applied with mechanical pressure for compaction, shaping or modelling.

In some embodiments, the first medium is deposited by a powder dispersion technique that comprises uses of shaking, controlled deposition, electrostatic deposition, dry powder deposition, powder deposition in a liquid that is a solvent of one of the first medium, the second medium, the third medium and the at least fourth medium, laser deposition, powder jet deposition, and electrospray.

In some embodiments, the second medium, the third medium and the at least fourth medium are deposited by a variety of methods that comprises electro-spraying, air deposition, bio-printing, extrusion, poring and curtain polymer deposition.

In some embodiments, the porosity of the scaffold is controlled by the deposition parameters, density of component materials and packing; and the porosity of the scaffold varies from 1 to 99%. In some embodiments, the porosity of the scaffold is tunable with pore sizes from 0.1 nm to 10 mm. In one embodiment, the size of the pores is between 0.1 nm to 3 mm. In other embodiments, the size of the pores can be between 0.1 nm to 1 mm, between 0.1 nm to 500 μm, between 0.1 nm to 200 μm, between 0.1 nm to 100 μm, between 0.1 nm to 50 μm, between 0.1 nm to 10 μm, between 0.1 nm to 5 μm, or between 0.1 nm to 1 μm.

In some embodiments, the surface area of the scaffold is between 0.001 and 5000 $m^2/g$. Preferably, the surface area of the scaffold is between 0.001 and 50 $m^2/g$, between 50 and 100 $m^2/g$, between 100 and 120 $m^2/g$, between 120 and 150 $m^2/g$, between 150 and 200 $m^2/g$, between 200 and 500 $m^2/g$, between 500 and 1000 $m^2/g$, or between 1000 and 5000 $m^2/g$.

In some embodiments, the scaffold is loaded with a plurality of cells, a plurality of drugs, or a plurality of growth factors.

In some embodiments, the scaffold is exposed to a gas plasma or corona discharge process in order to induce surface charges of positive, neutral, or negative polarity so as to increase the roughness of the surface morphology and introduce atoms and functional groups onto the surface.

In some embodiments, the scaffold is designed to have a non-uniform density and packing density.

In some embodiments, construction of the scaffold is done by using 3D bio-printing and hybrid printing technology by layer-by-layer deposition.

In some embodiments, the bone particles comprise human bone particles, animal bone particles, and/or artificial bone particles.

In some embodiments, the bone particles have sizes in a range between 1 nm to 100 mm.

In some embodiments, the polymer is a natural or synthetic biocompatible and/or biodegradable polymer.

In some embodiments, the first medium and the second medium are arranged in layers with the second medium arranged in horizontal or vertical geometries.

In some embodiments, the second medium is deposited in a pattern including a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

In some embodiments, the third medium comprises solid particulates that dissolve when immersed in liquid or gaseous solvent environments or based on temperature differentials and that do not immediately interact with the first medium and the second medium.

In some embodiments, the third medium is a single or a mixture of rapidly dissolving polymers in a solvent that immediately interacts with the first medium and the second medium.

In some embodiments, the third medium is a single rapidly dissolving polymer or a mixture of rapidly dissolving polymers in a solvent that does not immediately interact with the first medium and the second medium.

In some embodiments, the plurality of materials further comprise at least a fourth medium, and wherein the at least fourth medium material is a polymer with a faster or longer bio-degradation time in a biological system compared to the second medium.

In some embodiments, the at least fourth medium materials are loaded with a variety of solid particulates similar to the second medium or the third medium in weight ratios varying from 0.01 to 99.99 wt. %.

In some embodiments, each of the second medium, the third medium and the at least fourth medium has degradation rates ranging from 1 second to 100 months.

In some embodiments, the at least fourth medium is independent or along with the second medium and is deposited in equal or variable ratios compared to the second medium.

These and other aspects of the present invention are further described in the following section. Without intending to limit the scope of the invention, further exemplary implementations of the present invention according to the embodiments of the present invention are given below. Note that titles or subtitles may be used in the examples for the convenience of a reader, which in no way should limit the scope of the invention. Moreover, certain theories are proposed and disclosed herein; however, in no way should they, whether they are right or wrong, limit the scope of the invention so long as the invention is practiced according to the invention without regard for any particular theory or scheme of action.

Example 1

Materials:

Medium A includes a polymer or polymers combination of various ratios that are biocompatible, biodegradable, e.g., polyurethane, polyether urethane, PMMA, PGLA, PLLA, etc., or other biodegradable polymers. Medium A can be combined with ethanol, methanol, or other organic solvents or mixtures thereof.

Medium B includes soluble crystals, for example, sodium chloride, and sugar or any other medium that preferentially dissolves in a solvent before medium A does, such as a fast degrading biocompatible, biodegradable polymer such as polyvinylpyrrolidone, poly(vinyl alcohol), poly(ethylene glycol), etc.

Sieves with different mesh size.

A tool to shape the composite in various shapes: cylindrical, films, tubular, spherical, triangular, conical, etc. For example: syringes and needle with different size and diameter, 3D printer that can produce various shapes and dimensions, spray-systems such gas-flow, electrospray, etc.

Drying environments that allow the solvent to be removed, either under ambient conditions or variable temperatures, pressures and electromagnetic excitations.

Beakers and flasks, mortar and pestle.

Medium C includes hard material fillers that include structures or combination of structures with dimensions between 1 nm to 5 mm and which can include: gold, silver, copper and other metals, or a combination of them (micro- and nano-sized structures of various shapes nanospheres, nanorods, nanoplates, cylindrical, nanocubes, nanopyramids, nanocavities), graphitic materials (nanotubes, graphene, nanofibers, nanoonions, nanocones, etc.), hydroxyapatite (micro and nanosized), bone component particles and nanoparticles, calcium phosphate, ceramics of micro and nano sizes.

Medium D includes deionized (DI) water, sodium hydroxide, ethanol, methanol, or other organic solvents, or mixtures thereof.

Tissue regeneration enhancement drugs such as antimicrobials, anti-inflammatory, etc.

Growth factors, such as BMP, NGF, EGF, etc., proteins, DNA, RNA, extracellular matrix proteins.

Cells such as stem cells of various types, tissue specific cells, progenitors, etc.

Figure 2A:
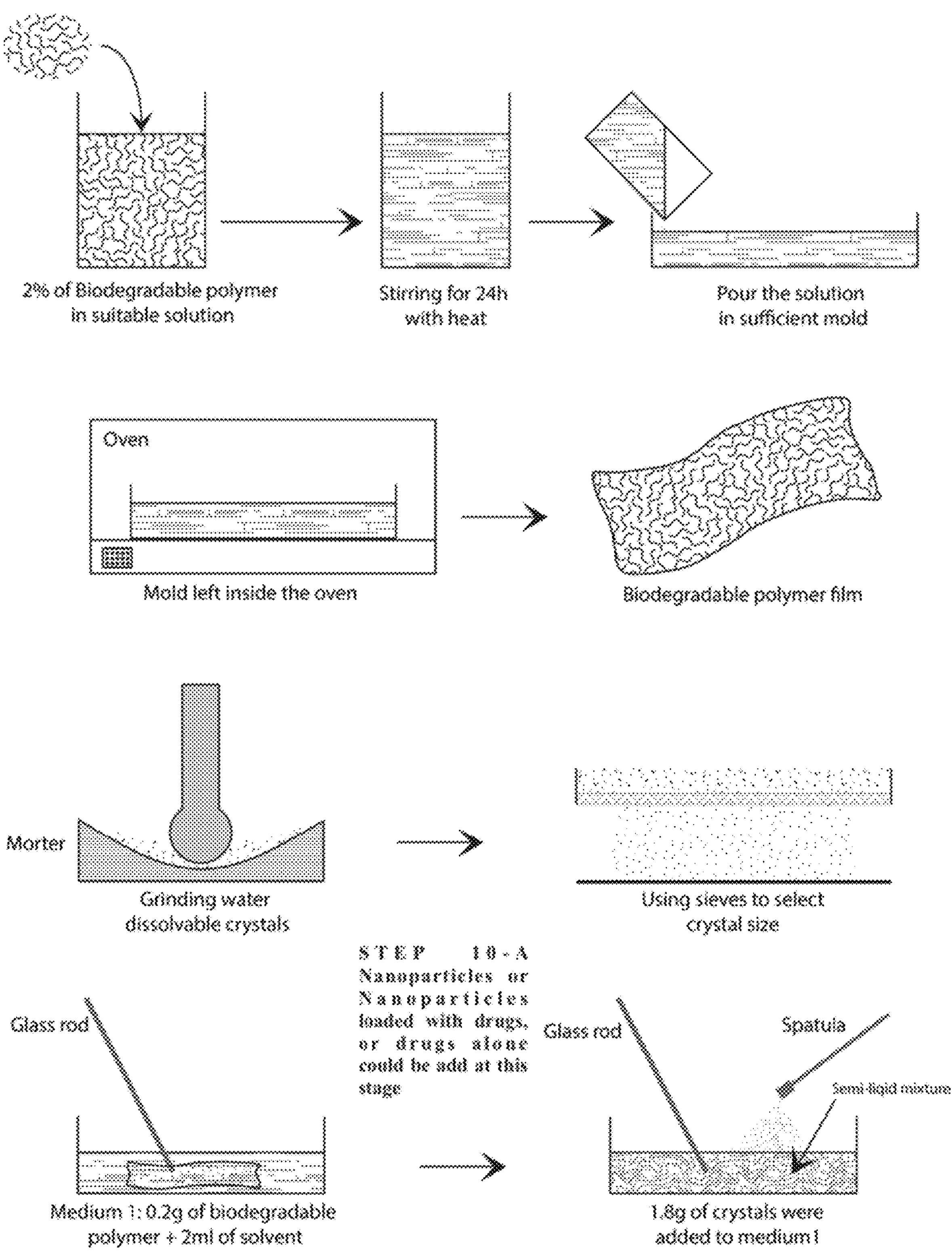
FIGS. 2A-2B show schematically processes (steps) for fabricating a biocompatible structure according to certain embodiments of the invention.
Figure 2B:
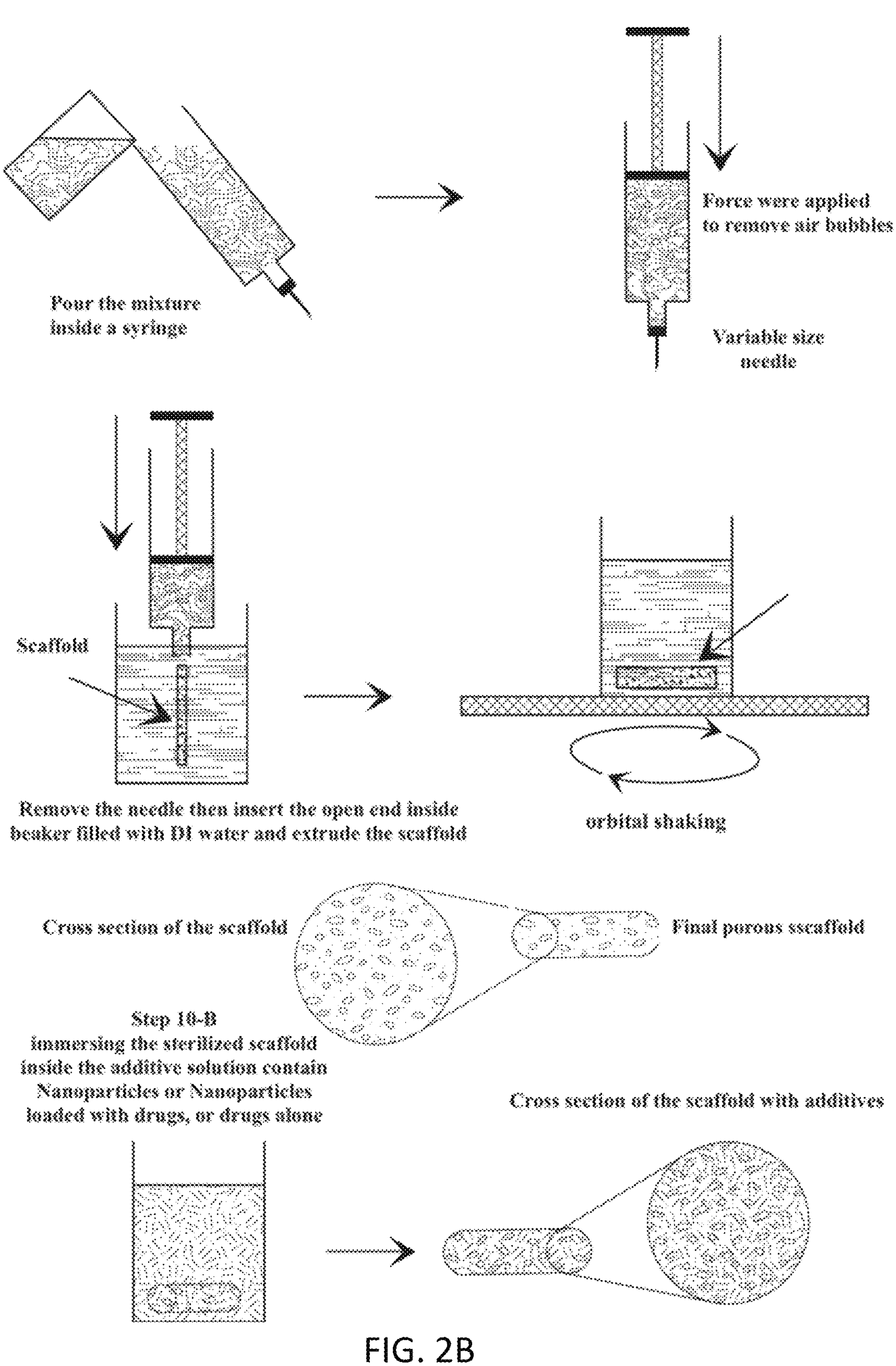

Method:

FIGS. 2A-2B show the method (steps/operations) for fabricating the scaffold according to the exemplary embodiment of the invention.

(1). Dissolving 2 g of polyurethane in 100 ml of 90% ethanol/10% DI water, leaving the solution under heat (60° C.) and stirring at 360 rpm for 48 hours. In general, different biodegradable and biocompatible polymers can be used in place of polyurethane. For example, in one embodiment, the biodegradable and biocompatible polymers are polyether urethanes. Of them, polyether polyurethane is less affected by cold temperatures. Polyurethanes can withstand sudden and dramatic temperature drops without cracking. And even at their highest hardness levels, polyurethanes have a better impact resistance than most plastics. The polymer amount used can also be changed through this step.

(2). Purging the mixture in a proper mold, and then keeping it inside a preheat oven with a specific temperature overnight.

(3). Grinding the soluble crystals by using the mortar and pestle, then selecting specific crystal size by using the sieves with different mesh size, for example crystals range from 75 to 150 μm. Crystal size can be altered depending on the design.

(4). To prepare medium A, cutting 0.2 g of previously prepared thin film and putting it inside the mortar, then adding 2 ml of absolute ethanol, waiting for suitable time till the polymer become very soft and easy to mix. Generally, component for medium A can be changed, depending on the type of biodegradable polymer used.

(5). Adding 1.8 g of soluble crystals medium B with selective crystal size to the mortar, then mixing it with the medium A until a paste-like state is achieved. In general, the mixing ratio between biodegradable polymer and the soluble crystals can be altered depend on the quantity of the porosity within the scaffold, in this mixture case around 90% porosity were achieved within the structure.

(6). Placing the mixture inside a syringe with desired size and diameter. Applying pressure by a syringe plunger to the mixture, in order to remove any bubbles. Generally, different tools can be used to shape the composite in various shapes.

(7). Extruding the mixture by using the syringe inside a beaker contain DI water medium D, where the polymer solidifies once it comes in contact with water and it take the shape and size of open end of the syringe. Generally, scaffold dimension range from 0.5 nm to 30 cm. DI water can be altered with other liquids.

(8). Gently transferring the scaffold in a water bath that is placed on an orbital shaker. Keeping the scaffold for suitable period inside the water bath under orbital shake to allow leaching of the soluble crystals with DI water; exchanging DI water once every 10 to 12 hours, this process is continues till the soluble crystals are totally removed from the structure.

(9). After a complete leaching of solvent dissolvable crystals, placing the scaffold under vacuum until completely dry. Sterilization is accomplished by washing it twice with 1× PBS and DI water followed by exposure to UV light overnight.

(10). Incubating or incorporating nanoparticles and tissue regeneration enhancing drugs within the scaffold. The step can be performed as follows:

(A) Direct addition of the nanoparticles, microparticles, nanoparticles or microparticles loaded with drugs, or drugs alone within the mixture prepare by step (5), followed by next normal steps.

(B) Loading the nanoparticles, microparticles which can be loaded with drugs, cells, etc. within the scaffold is accomplished by immersing the sterilized scaffold inside the solution contain nanoparticles or nanoparticles loaded with drugs, or drugs alone cells, etc., for a specific period.

In certain aspects, the invention relates to a system to develop multifunctional scaffolds for bone regeneration based on the following descriptions.

The system is composed in 3D by alternating layers of various materials listed as media A-D such that the final dimensions and shape meet the needs of the volume of bone to be regenerated. The system can be arranged in the shape and size of a bone gap that needs to be regenerated, as developed by a 3D CT scanner.

Example 2

Materials:

A first medium (or medium 1) includes one or more of the following materials: bone particles of human (such as Puros, Tutobone, Tutoplast, Osseo Plus, or similar/equivalent), or bone particles of animal origin (bovine such as BioOss, Botiss, InterOss, NuOss or similar/equivalent, or porcine such as MatrixOss or similar/equivalent), or artificial bone particles grown in the laboratory (demineralized and/or decellularized), hydroxyapatite, beta or alpha-tricalcium phosphate, calcium phosphate, carbonate apatite, bone chips, etc. The sizes of the bone particles can be in a range of between about 1 nm to about 100 mm. The bone particles can be with or without organic components such as collagen or similar structures.

A second medium (or medium 2) includes one or more of the following materials: a natural or synthetic biocompatible and/or biodegradable polymer, such as polyurethanes, polyether urethanes, polylactide (PLA), polyglycolide (PGA), poly(lactide-co-glycolide) (PLGA), poly(e-caprolactone), polyanhydride, trimethylene carbonate, poly (trimethylene carbonate), poly(β-hydroxybutyrate), poly(g-ethyl glutamate), polydioxanone (PDO), poly(desaminotyrosine-tyrosylhexyl ester iminocarbonate) (poly(DTH iminocarbonate)), poly(bisphenol A iminocarbonate), poly(ortho ester), polycyanoacrylate, polyphosphazene, poly(α-esters), poly(L-lactic acid) (PLLA), poly(D-lactic acid) (PDLA), poly(D, L-lactic acid) (PDLLA), polyhydroxyalkanoates, poly (3-hydroxybutyrate), poly(3-hydroxybutyrate-co-3-hydroxyvalerate) (PHBV), polycaprolactone (PCL), poly(propylene fumarate) (PPF), polyacetals, poly(ortho esters), polycarbonates, (PTMC), poly(desaminotyrosyltyrosine alkyl ester carbonates) (PDTE), (poly[bis(trifluoroethoxy) phosphazene], polyphosphoesters, polyesters, poly(β-amino esters) (PBAE), poly(anhydride ester), poly(ester urethane), poly(ethylene glycol) (PEG), poly(propylene glycol) (PPG), triblock Pluronic® ([PEG]n-[PPG]m-[PEG]n), poloxamer (i.e., an amphiphilic copolymer composed of a central hydrophobic chain of polyoxypropylene (poly-propylene oxide) flanked by two hydrophilic chains of polyoxyethylene (polyethylene oxide)), PEG diacrylate (PEGDA), PEG dimethacrylate (PEGDMA), Collagen (e.g., Collagen types I, II, III and IV), elastin and elastin-like polypeptides (ELPs), albumin, fibrin, natural poly(amino acids), poly(γ-glutamic acid), poly(L-lysine), synthetic poly(amino acids), poly (L-glutamic acid), poly (aspartic acid), poly (aspartic acid) (PAA), polysaccharides, hyaluronic acid (HA), chondroitin sulfate (CS), polycaprolactone (PCL), chitin, chitosan, alginate, dextran, agarose, mannan and/or inulin.

In certain embodiments, the natural or synthetic biocompatible and/or biodegradable polymer of the second medium is configured to be dissolved or removed in a first solvent. The natural or synthetic biocompatible and/or biodegradable polymer can be mixed/doped with one or multiple dopants such as the bone particles of the first medium with dimensions from about 1 nm to about 10 mm, and/or a third medium that can be dissolved or removed in a second solvent that is different than the first solvent of the natural or synthetic biocompatible and/or biodegradable polymer used.

A third medium (or medium 3) includes medium 3*a* and/or medium 3*b* containing solid particulates alone or in polymeric structures. Medium 3*a* can be solid particulates such as NaCl, chloride, sugar (alone or in polymeric structures) or other powders that can dissolve when immersed in liquid or gaseous solvent environments (i.e., the second solvent) or based on temperature differentials, which the liquid or gaseous solvent environments do not immediately interact with the second medium. Medium 3*b* can be a single or a mixture of rapidly dissolving polymers (such as polyvinylpyrrolidone (PVP), or other fast degrading polymers) in the second solvent that does or does not immediately interact with the first medium, the second medium or other materials used.

In certain embodiments, the solid particulates alone or in polymeric structures are dissolvable or removable in the second solvent that is different from the first solvent. In some embodiments, the solid particulates have a rate of degradation or dissolution that is faster than that of medium 2 in the second solvent. In some embodiments, the solid particulates are adapted for producing pores in the 3D structure of the scaffold after they are dissolvable or removable. The sizes of the solid particulates determine the pore sizes of the scaffold, while the concentration of the solid particulates in a composition containing the first, second and third media with which the scaffold is formed determines the porosity of the scaffold, which is the proportion of pore volume in the total volume of the scaffold, and a dimensionless value that, for example, can vary from 1% to 99%, according to the invention. The former (the porosity of the scaffold being 1%) indicates the concentration of the solid particulates in the composition is much less than the concentrations of the first medium and the second medium, i.e., the composition has few the solid particulates alone or in polymeric structures, while the latter (the porosity of the scaffold being 99%) indicates the concentration of the solid particulates in the composition is much greater than the concentrations of the first medium and the second medium, i.e., the solid particulates dominate in the composition. Accordingly, according to the invention, the pore sizes and porosity of the scaffold are operably tunable by changing the sizes and concentration of the solid particulates of the third medium in the composition.

Additionally, a multitude of materials including, but are not limited to, a fourth medium (medium 4), a fifth medium (medium 5), and/or sixth medium (medium 6), is used, which are polymers with a faster or longer bio-degradation time in a biological system (in vivo or in vitro biological system) compared to that of the second medium in the biological system. These materials can be similarly loaded with a variety of solid particulates (the second medium or the third medium) in weight ratios varying from 0.01 to 99.99 wt. %, where the former (0%) indicates the composition do not have the multitude of materials, while the latter (99.99%) indicates the multitude of materials dominates in the composition. The polymers, e.g., the second, third, fourth, fifth, sixth media, etc. can have degradation rates ranging from 1 second to 100 months.

Figure 3:
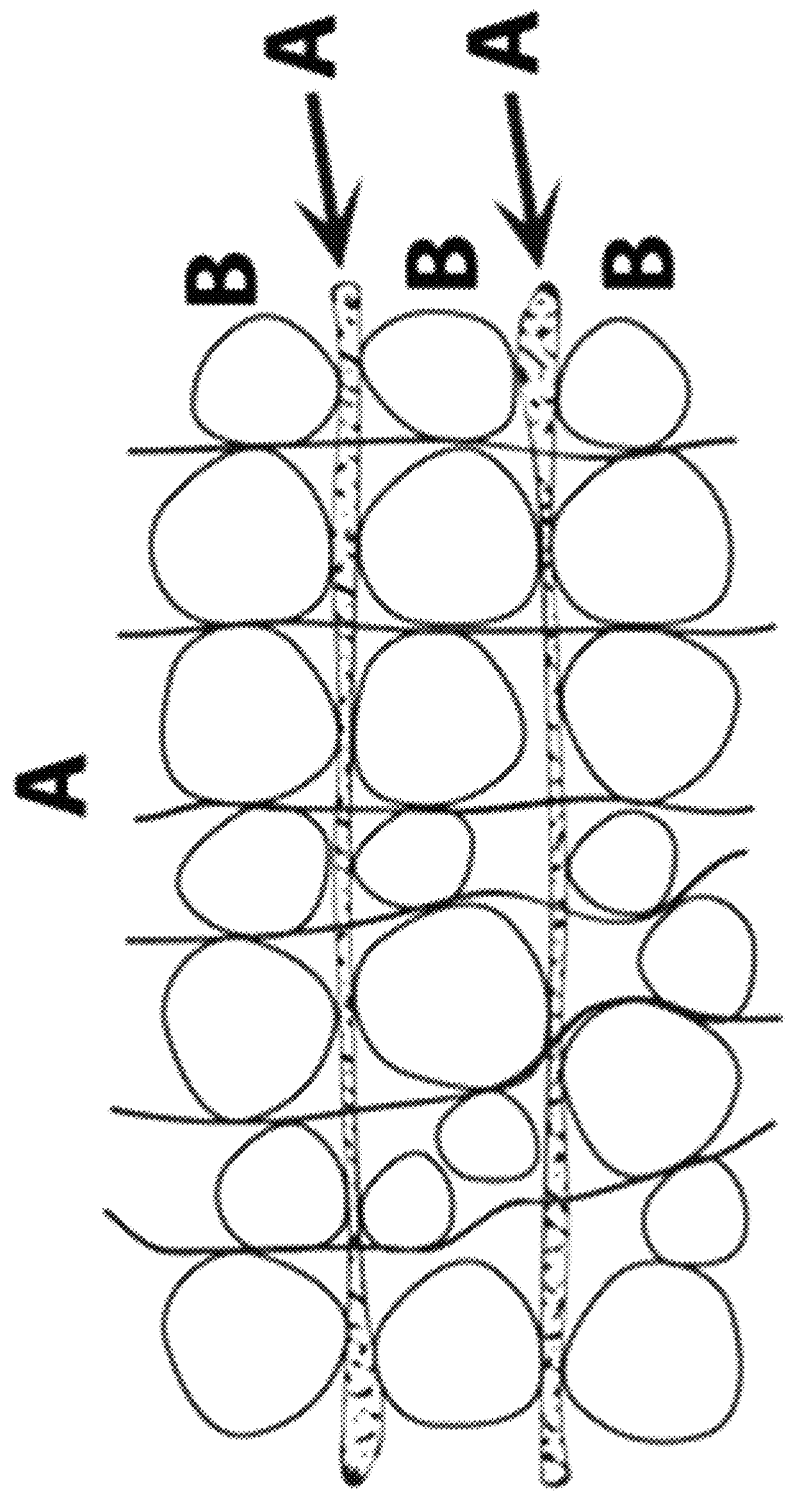
FIG. 3 shows schematically 3D structure of a biocompatible structure according to certain embodiments of the invention: A: the first medium, and B: the second medium with or without the third medium included.

The arrangement of the first medium with the second medium can be done in layers, as shown in FIG. 3, with the second medium being arranged in horizontal or vertical geometries. Specifically, FIG. 3 shows one embodiment of the scaffold: A: the first medium, and B: the second medium with or without the third medium included. The first medium labelled as "A" are disposed to separate the second medium horizontally and/or vertically.

FIGS. 4A-4G show patterns of possible deposition of various media. Some of these geometries in which the second medium can be deposited are shown in FIGS. 3 and 4A-4G. The thickness of the film of the second medium film ranges from 1 nm to 10 mm. In FIG. 4A, the geometry is a continuous u-shaped line that has a repeatable pattern. The repeatable pattern has a first half circle, a first straight line connected to the first half circle and a second half circle opposed to the first half circle and a second straight line connected to the second half circle. In FIG. 4B, the pattern is a rectangle. In FIG. 4C, the pattern includes a continuous u-shaped line that has two patterns of FIG. 4A, but the two patterns of FIG. 4A in FIG. 4C are orthogonal to each other. In FIG. 4D, the pattern has a plurality of irregular circular-shaped media. In FIG. 4E, the pattern has a plurality of horizontal lines and a plurality of vertical lines. The plurality of horizontal lines and the plurality of vertical lines form a plurality of square-shaped patterns of various media. In FIG. 4F, different from FIG. 4D, the pattern includes a first plurality of lines and a second plurality of lines, and the first plurality of lines and the second plurality of lines form a quadrilateral shape of various media. In FIG. 4G, the pattern includes a plurality of hexagonal shapes.

Independent or along with the second medium, the third, fourth, fifth and sixth media, etc. can be deposited in equal or variable ratios compared to the second medium.

Deposition Method:

The deposition of all the media can be done as follows:

a) the first medium can be deposited by a powder dispersion technique that includes, but is not limited to, the use of shaking, controlled deposition, electrostatic deposition, dry powder deposition, powder deposition in a liquid (which can be the solvent of either one of the media 2, 3, 4, 5, 6, etc.), laser deposition, powder jet deposition, electrospray, etc.;

b) the second, third, fourth, fifth and sixth media, etc., can be deposited by a variety of methods that include, but is not limited to, electrospraying, air deposition, bioprinting, extrusion, poring, curtain polymer deposition, or other methods that result in the architectures and sizes that are desired. The deposition system can have multiple single nozzles that are all controlled individually by a pre-designed computer controlled process;

c) it is possible for the successive layers to be mechanically modeled into various shapes and mechanical pressure to be applied for compaction, shaping or modelling; and d) the ultimate porosity is controlled by the deposition parameters, density of component materials, packing, etc., but the pore sizes are between about 0.1 nm to about 3 mm. The actual porosity of the 3D structure can vary from 1% to 99% by volume of the 3D structure.

In some embodiments, the scaffold can be loaded with a variety of cells such as osteoblasts, osteoclasts, stem cells, mesenchymal stem cells, osteocytes, etc.

In some embodiments, the scaffold can be loaded with a variety of drugs (single or combinations) such as antibiotics that include, but are not limited to, Cefazolin, Cefuroxime, Flucloxacillin and gentamicin, Ceftriaxone, Clindamycin, Vancomycin, ciprofloxacin, tigecycline, tobramycin, Piperacillin, tazobactam and lovastatinetc. The loading ratios of the antibiotics can be varied from 0 to the maximum loading capacity. The antibiotic uptake can take place in the porosity of the scaffold or in the structure of the polymers used in the construction of the scaffold.

The scaffold can be loaded with anti-cancer drugs (one or multiple) that include but are not limited to, Doxorubicin (Adriamycin), Mitotane, Cisplatin, Carboplatin, Etoposide (VP-16), Ifosfamide (Ifex), Cyclophosphamide (Cytoxan), Vincristine (Oncovin), Abitrexate (Methotrexate), Cosmegen (Dactinomycin), Doxorubicin Hydrochloride, Folex (Methotrexate), Folex PFS (Methotrexate), Methotrexate, Methotrexate LPF (Methotrexate), Mexate (Methotrexate), Mexate-AQ (Methotrexate), Xgeva (Denosumab), Vincristine, ifosfamide, doxorubicin, etoposide (VIDE), Vincristine, actinomycin and ifosfamide (VAI), Vincristine, actinomycin D (dactinomycin) and cyclophosphamide (VAC), Methotrexate (Maxtrex), Etoposide (Eposin, Etopophos, Vepesid), Ifosfamide (Mitoxana), Docetaxel (Taxotere), Gemcitabine (Gemzar), Carboplatin (Paraplatin), Irinotecan Campto), Temozolomide (Temodal), Topotecan (Hycamtin, Potactasol), paclitaxel, Granulocyte colony stimulating factor (G-CSF), 5-fluorouracil, Actinomycin D (dactinomycin, Cosmegen). The loading ratios of the drugs can be varied from 0 to the maximum loading capacity. The drug uptake can take place in the porosity of the scaffold or in the structure of the polymers used in the construction of the scaffold.

The scaffold can be loaded with a variety of growth factors (one or multiple) that include, but are not limited to: platelet-rich plasma (PRP), platelet-derived growth factor (PDGF), vascular endothelial growth factor (VEGF), fibroblast growth factor (FGF), Dorsalin-1, GDF-1, GDF-3, GDF-8, GDF-9, GDF-12, GDF-14, IGF-I, IGF-II, TGF-p, TGF, BMP-Sb, BMP-2, BMP-3, BMP-4, BMP-5, BMP-6, BMP-7, BMP-8, BMP-9, BMP-10, BMP-11, BMP-12, BMP-13, BMP-14, BMP-15, deoxyribonucleic acid (DNA), ribonucleic acid (RNA), plasmids, proteins, or a mixture thereof, wherein BMP is bone morphogenetic protein, GDF is growth differentiation factor, IGF is insulin growth factor, and TGF is transforming growth factor.

The scaffold can be exposed to a gas (nitrogen, oxygen, helium, argon, or mixtures, etc.) plasma/corona discharge process in order to induce surface charges of positive, neutral, or negative polarity. The process can be used to increase the roughness of the surface morphology and introduce atoms and functional groups onto the surface.

The scaffold can be designed to have a non-uniform density and packing density. As an example, the density at the edges can be higher or lower compared to the interior.

In certain embodiments, the construction/fabrication of the scaffold can be done by using 3D bio-printing and hybrid printing technology by layer-by-layer deposition (the 3D architecture as shown in FIG. 3). Multi-nozzle deposition system can be used for the media 1, 2, 3, 4, 5, 6, etc. Dual nozzles can be used such that one nozzle is inside of another nozzle concentrically or eccentrically, where the diameter/size of the output tip of the outer extruder nozzle is larger than that of the inner extruder nozzle, as shown in FIGS. 5A, 6A, 7A and 8. The diameters/sizes of the output tips of the inner and outer extruder nozzles may determine the thicknesses of the corresponding layers. Larger diameters/sizes may result in thicker layers. In addition, different shapes of the output tips and/or different routines and patterns along which the output tips move may result in different morphologies/profiles of the scaffolds.

Figures 5A, 5B, 5C, 5D, 5E:
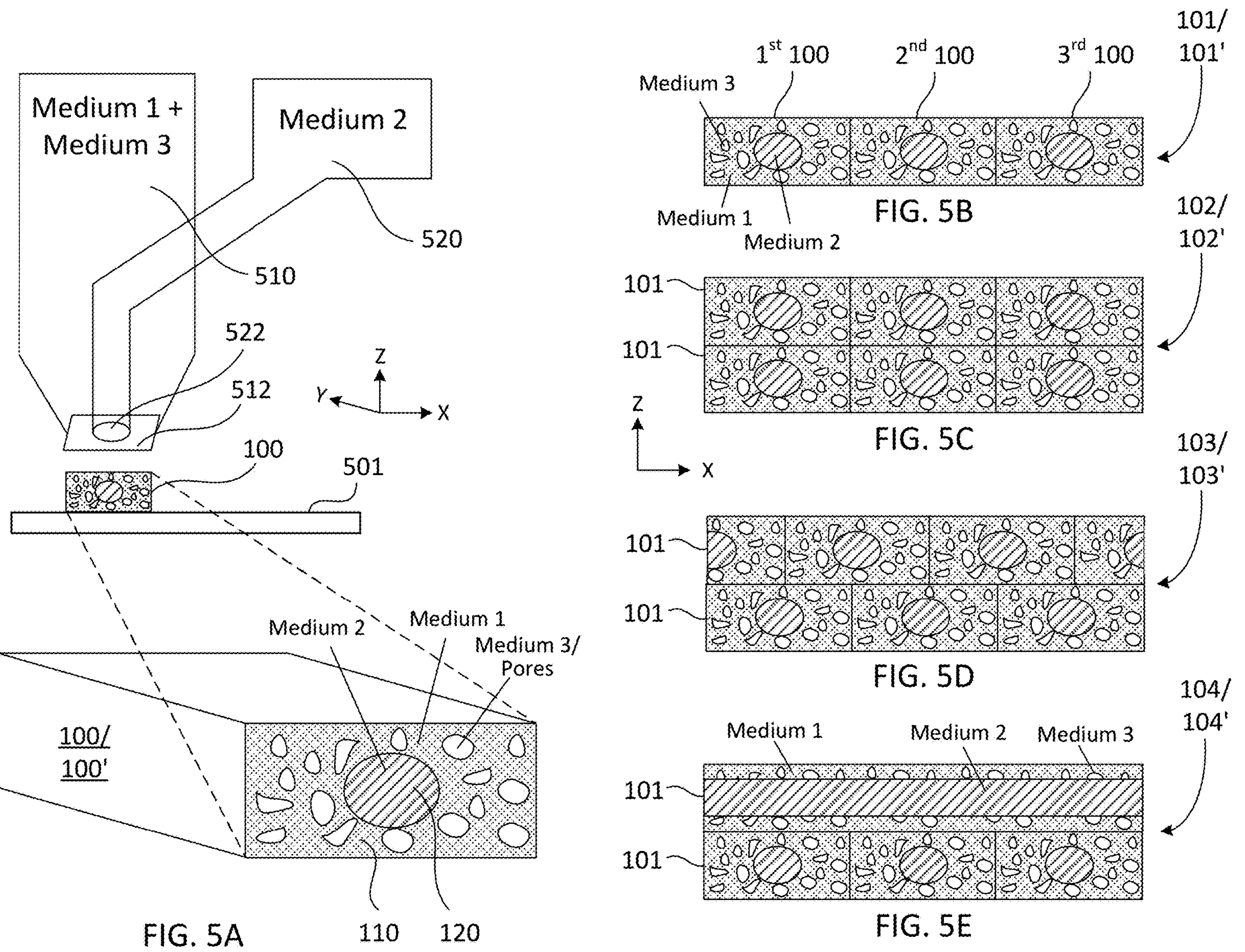
FIG. 5A shows schematically a nozzle arrangement for the co-deposit first, second and third media according to certain embodiments of the invention.
FIGS. 5B-5E shows schematically 3D structures/scaffolds of a biocompatible structure according to certain embodiments of the invention.

Specifically, FIG. 5A shows one exemplary arrangement of the dual nozzles to co-deposit the first medium, the second medium and the third medium. The dual nozzles include a first nozzle 510 having an output tip 512 and a second nozzle 520 having an output tip 522 that is concentrically aligned inside of the output tip 512 of the first nozzle 510. The output tip 512 has a rectangle shape while the output tip 522 has a circle shape. It should be noted that other shapes of the output tips can also be used to practice the invention. In this exemplary embodiment shown in FIG. 5A, the first nozzle 510 contains the first medium and the third medium, while the second nozzle 520 contains the second medium. The first nozzle 510 and the second nozzle 520 are concentrically aligned to deposit the first medium, the second medium and the third medium onto a sample stage 501, thereby forming a base layered structure 100 on the sample stage 501, as shown in FIG. 5A. The base layered structure 100 includes a first layer 110 of the first medium (medium 1) and the third medium (medium 3), and a second layer 120 of the second medium (medium 2) that is surrounded by the first layer 110. That is, the base layered structure 100 has co-extruded first layer 110 and second layer 120 with different materials/media from each other. After the third medium (medium 3) is dissolved or removed in a second solvent from the base layered structure 100, a scaffold 100' is formed to have the first medium (i.e., the bone particles) and the pores (i.e., the spaces left after the solid particulates of the third medium are dissolved or removed) in the first layer 110 and the second medium (i.e., the natural or synthetic biocompatible and/or biodegradable polymer) in the second layer 120.

Accordingly, various scaffolds can be formed by assembling a plurality of the base scaffolds 100' according to different designs. For example, attaching a predetermined number of the base scaffolds 100' to each other along a horizontal direction can form a first scaffold (e.g., FIG. 5B). Attaching another predetermined number of the base scaffolds 100' to each other over the first scaffold along the same direction, or different directions may form a second scaffold (FIG. 5C), or other scaffolds (FIGS. 5D-5E).

In addition, by moving the sample stage 501 and/or the dual nozzles according to predetermined routines, various scaffolds with different patterns and layouts can also be fabricated. For the illustration purpose, the dual nozzles are moved according to the predetermined routines in the fabricating processes of the following exemplary embodiments of the scaffold. It should be noted moving the sample stage 501 or moving both the dual nozzles and the sample stage 501 can also be utilized to practice the invention. For example, in one embodiment shown in FIG. 5B, the 3D structure 101 includes three base layered structures 100 laterally aligned along one another, which can be achieved by translationally moving the dual nozzles over the sample stage 501. For example, (1) moving the dual nozzles along a first direction (e.g., the Y direction shown in FIG. 5A) and meanwhile extruding the first, second and third media therefrom forms a first base layered structure 100 (i.e., 1$^{st}$ 100 in FIG. 5B), (2) moving the dual nozzles next to the first base layered structure 100 along a second direction (e.g., the X direction shown in FIG. 5A) perpendicular to the first direction, (3) moving the dual nozzles along a third direction (e.g., opposite the Y direction shown in FIG. 5A) and meanwhile extruding the first, second and third media therefrom forms a second base layered structure 100 (i.e., 2$^{nd}$ 100 in FIG. 5B), (4) moving the dual nozzles next to the second base layered structure 100 along the X direction, and (5) moving the dual nozzles along the Y direction and meanwhile extruding the first, second and third media therefrom forms a third base layered structure 100 (i.e., 3$^{rd}$ 100 in FIG. 5B). Furthermore, the treatment of the 3D structure 101 with a solvent to dissolve or remove or eliminate the solid particulates of the third medium are dissolved or removed) in the first layer 110 results in the scaffold 101' including three base scaffold 100' each have the first medium (i.e., the bone particles) and the pores in the first layer and the second medium (i.e., the natural or synthetic biocompatible and/or biodegradable polymer) in the second layer.

FIG. 5C shows another embodiment of the scaffold 102' that includes two scaffold 101' vertically stacked on one another. The fabricating processes of the scaffold 102' are same as that of the scaffold 101', except that the dual nozzles may need moving along the Z direction between fabricating the two 3D structures 101 so that the two 3D structures 101 are stacked on one another to form the 3D structure 102. After the treatment of the 3D structure 102 with a solvent to dissolve or remove or eliminate the solid particulates of the third medium are dissolved or removed) in the first layer results in the scaffold 102' including two scaffolds 101' stacked on one another.

FIG. 5D shows yet another embodiment of the scaffold 103' that includes two scaffold 101' vertically stacked on one another, which is same as the scaffold 102' of FIG. 5C, except that two scaffold 101' are shifted to each other long the X direction.

FIG. 5E shows one embodiment of the scaffold 104' that includes two scaffold 101' vertically stacked on one another, which is same as the scaffold 102' of FIG. 5C, except that two scaffold 101' are aligned perpendicularly to each other.

Furthermore, as shown in FIGS. 5B-5E, the 3D layered structures includes a plurality of base layered structures attached to each other horizontally and/or vertically and have no need to incorporate one or more polymer columns into the 3D layered structures 101-104 horizontally and/or vertically for adding rigidity to the 3D layered structures. Accordingly, the scaffolds 101'-104' of the invention contain no polymer columns horizontally and/or vertically.

It should be appreciated that other shapes of the output tips and/or other routines and patterns along which the dual nozzles move can also be utilized to practice the invention. For example, the dual nozzles may move along circles or zig-zags, or a pattern shown in FIG. 4, which includes a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

Figures 6A, 6B:
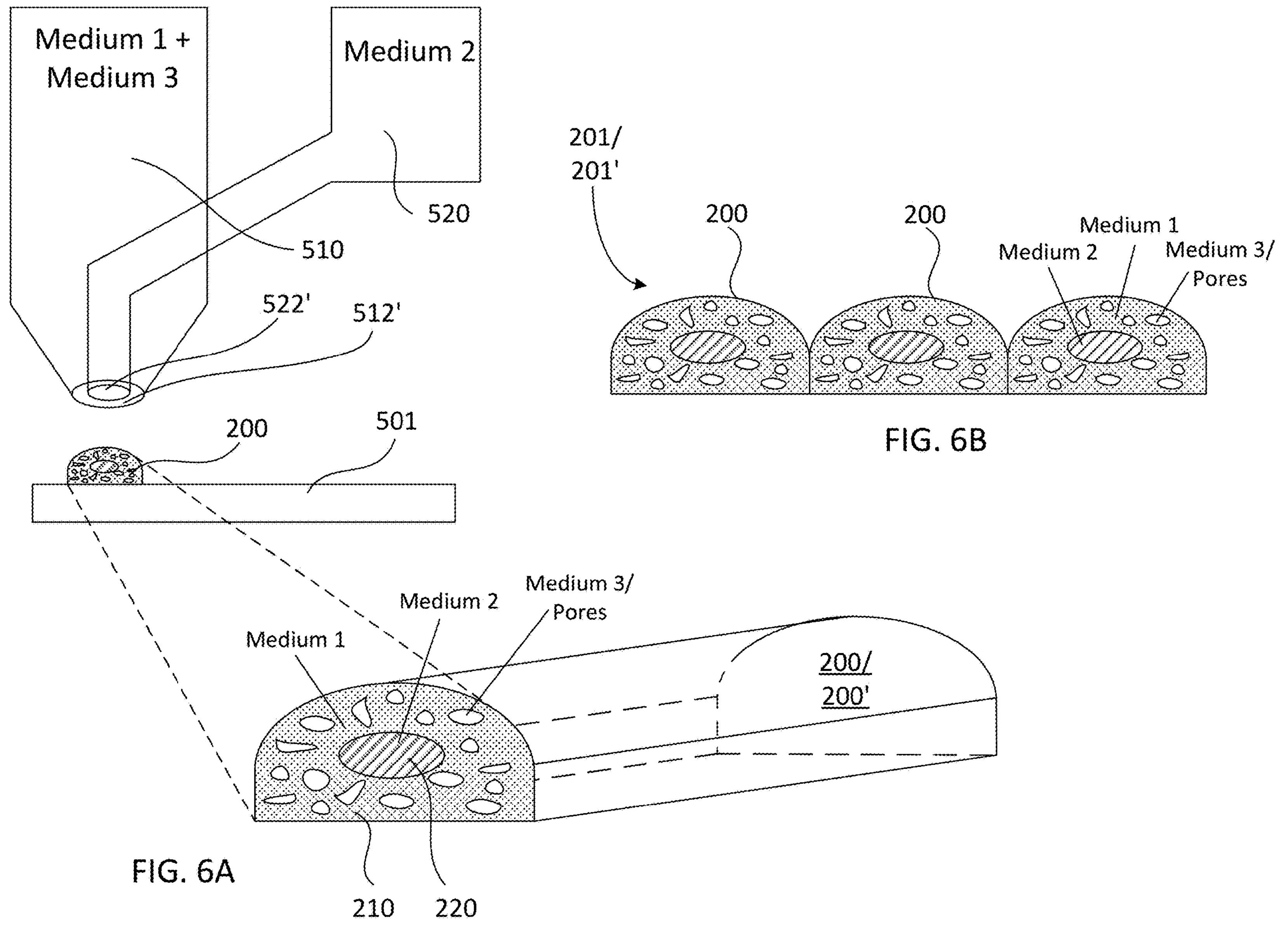
FIG. 6A shows schematically a nozzle arrangement for the co-deposit first, second and third media according to certain embodiments of the invention.
FIG. 6B shows schematically 3D structures/scaffolds of a biocompatible structure according to certain embodiments of the invention.

FIG. 6A shows a deposition system with multiple nozzles similar to that in FIG. 5A, except that both the output tips 512' and 522' of the outer and inner extruder nozzles 510 and 520 have circle shapes that are concentrically aligned to deposit the first medium, the second medium and the third medium onto the sample stage 501. The nozzle 510 contains the first medium and the third medium, and the nozzle 520 contains the second medium. The above discussed fabricating processes in relation to FIGS. 5A-5E can be applied to obtain/form the base layer structure 200 and the corresponding scaffold 200' (FIG. 6A), the scaffold 201/201' (FIG. 6B), and other scaffolds. The base layer structure 200 includes a first layer 210 of the first medium (medium 1) and the third medium (medium 3), and a second layer 220 of the second medium (medium 2) that is surrounded by the first layer 210. The base layer structure 200 has a curved outline profile resulted from the circled output tip 512' of the outer extruder nozzle 510. After the third medium (medium 3) is dissolved or removed in a second solvent from the base layered structure 200, the corresponding scaffold 200' is obtained, which has the first medium (i.e., the bone particles) and the pores (i.e., the spaces left after the solid particulates of the third medium are dissolved or removed) in the first layer 210 and the second medium (i.e., the natural or synthetic biocompatible and/or biodegradable polymer) in the second layer 220. The base scaffold 200' has a curved outline profile, as shown in FIG. 6A.

Figures 7A, 7B, 7C, 7D, 7E:
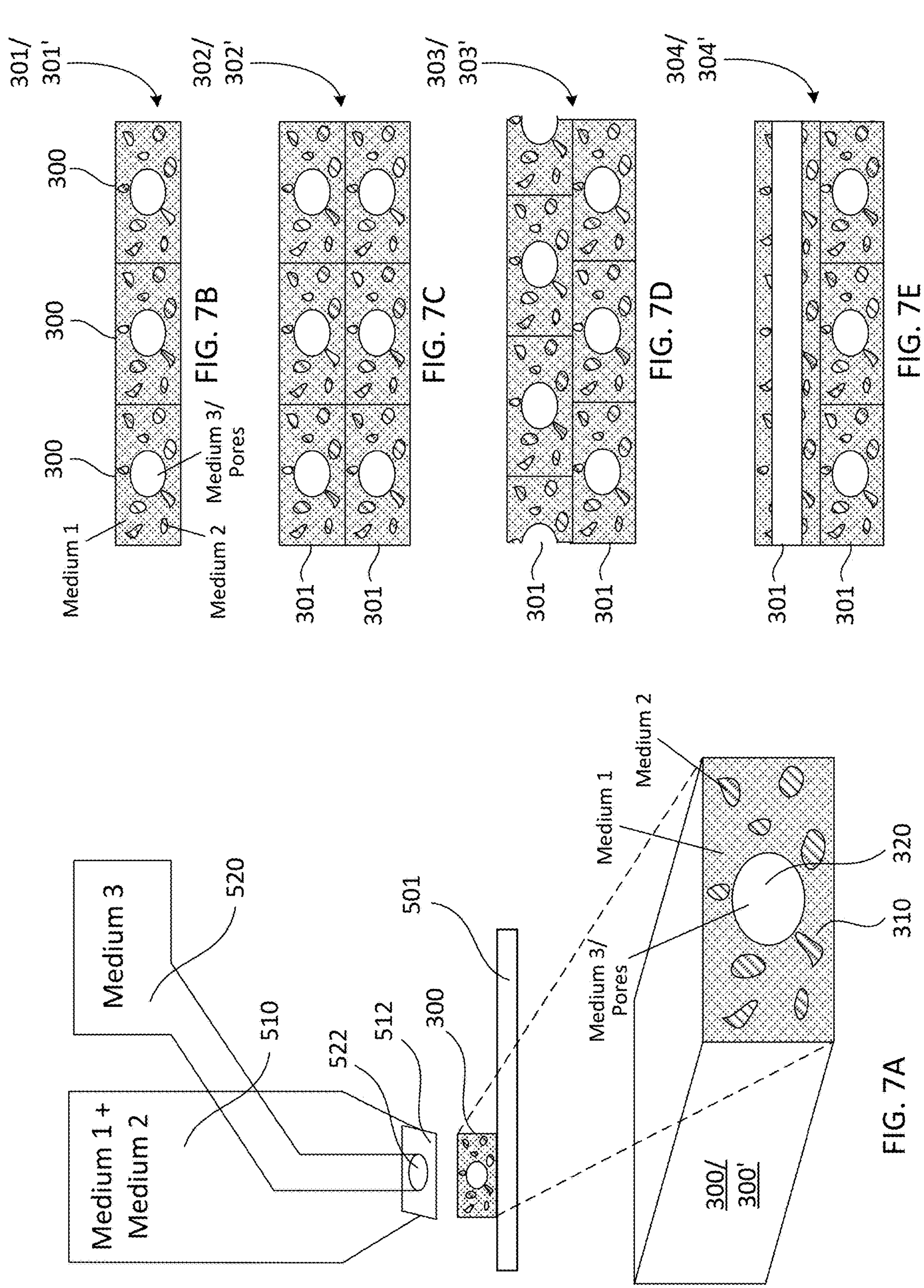
FIG. 7A shows schematically a nozzle arrangement for the co-deposit first, second and third media according to certain embodiments of the invention.
FIGS. 7B-7E shows schematically 3D structures/scaffolds of a biocompatible structure according to certain embodiments of the invention.

FIG. 7A shows the deposition system with multiple nozzles identical to that in FIG. 5A, except that the nozzle 510 contains the first medium and the second medium, and the nozzle 520 contains the third medium. The above discussed fabricating processes in relation to FIGS. 5A-5E can be applied to obtain/form the base layer structure 300 and the corresponding scaffold 300' (FIG. 7A), and the scaffolds 301/301' (FIG. 7B), 302/302' (FIG. 7C), 303/303' (FIG. 7D), and 304/304' (FIG. 7E). The base layer structure 300 includes a first layer 310 of the first medium (medium 1) and the second medium (medium 2), and a second layer 320 of the third medium (medium 3) that is surrounded by the first layer 310. After the third medium (medium 3) is dissolved or removed in a second solvent from the base layered structure 300, the corresponding scaffold 300' is obtained, which has the first medium (i.e., the bone particles) and the second medium (i.e., the natural or synthetic biocompatible and/or biodegradable polymer) in the first layer 310, and pores (i.e., the spaces left after the solid particulates of the third medium are dissolved or removed) in the second layer 320.

Figure 8:
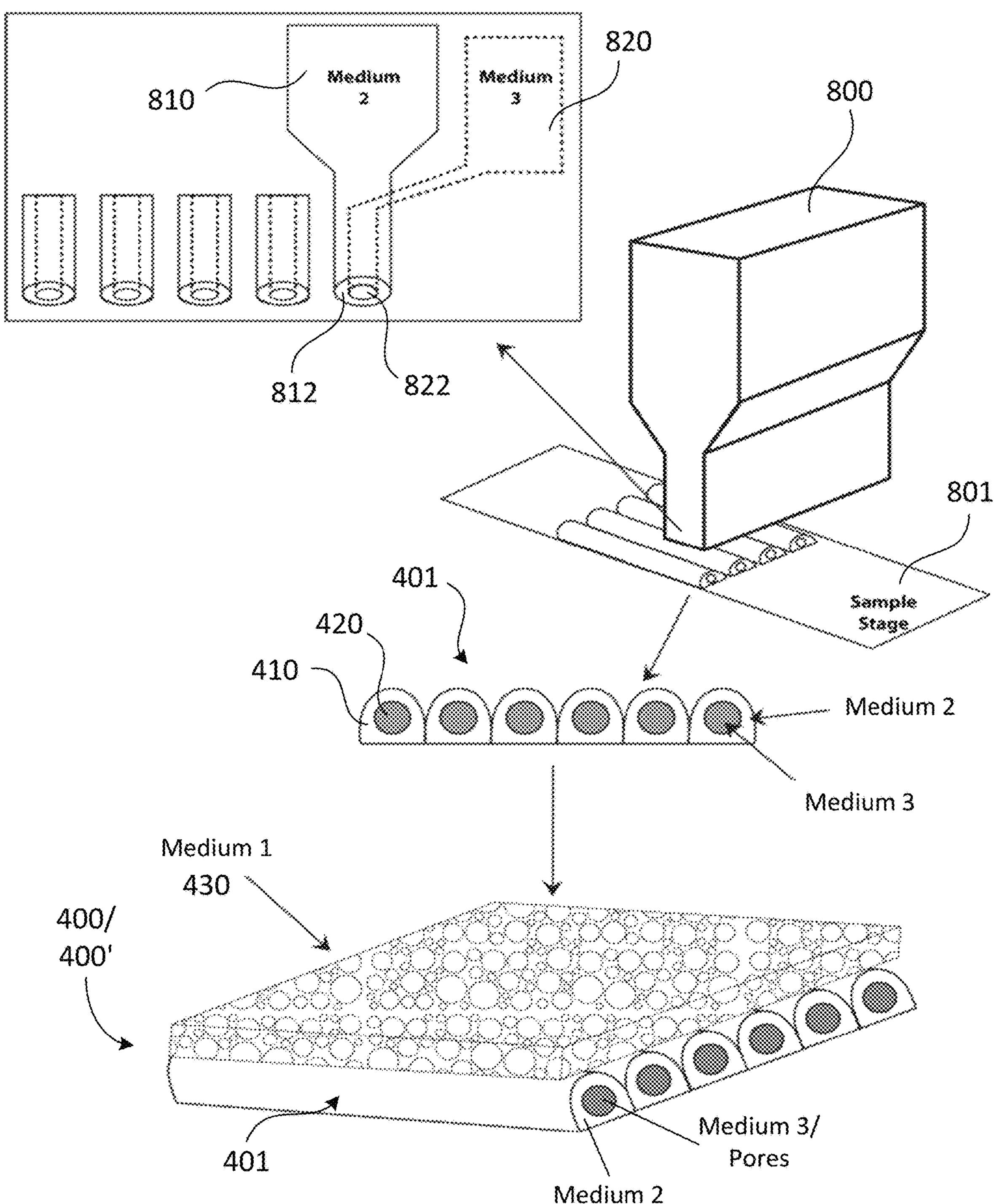
FIG. 8 shows schematically a deposition system with multiple nozzles and a corresponding 3D structure/scaffolds of a biocompatible structure according to certain embodiments of the invention.

FIG. 8 shows a deposition system 800 with multiple nozzles according to one embodiment of the invention. In this exemplary embodiment, the deposition system includes a plurality of dual nozzles aligned to each other. Each dual nozzles include a first nozzle 810 having an output tip 812 and a second nozzle 820 having an output tip 822 that is concentrically aligned inside of the output tip 812 of the first nozzle 810. Each of the output tips 812 and 822 has a circle shape. The first nozzle 810 contains the second medium, while the second nozzle 820 contains the third medium. In operations, the first nozzle 810 and the second nozzle 820 are concentrically aligned to deposit the second medium and the third medium onto a sample stage 801, thereby forming a base layered structure 401 on the sample stage 801. The base layered structure 401 includes a plurality of layered units, each unit having a first layer 410 formed of the second medium and a second layer 420 formed of the third medium. The second layer 420 is surrounded by the first layer 410, that is, the second medium and the third medium are concentrically aligned in each layered unit. A bone particles layer 430 formed of the first medium is disposed on the top of the base layered structure 401 to form a layered 3D structure 400. After the treatment of the layered 3D structure 400 with a solvent to dissolve or remove or eliminate the third medium, the layered scaffold 400' with pores defined by the spaces of the third medium in the layered 3D structure 400 is obtained.

In some embodiments, the nozzles or extruders are controlled independently from each other so that, for example, more materials can be extruded from the outer extruder compared to inner extruder or vice versa. The various extruders deposit the second medium, the third medium, the fourth medium, etc., with various concentrations of medium 3*a* or medium 3*b*. For example, it is envisioned to have low concentration salt-printing media 3*a* and 3*b* mixture in the outer extruder and high concentration salt-printing material into the inner extruder. In this method by controlling the third medium to material ratio and the nozzle sizes, it is possible to control the pore size and their distribution while 3D printing the scaffold.

In some embodiments, a 3D file (such as, but not limited to, CAD) of the bone can be designed so that the bone is printed by the 3D position system including printer or bioprinter. This CAD design includes information to use extruders automatically while printing different layers to mimic the natural bone architecture.

To produce bone layer with less pores the outer extruder prints more material compared to the inner extruder, whereas to produce bone layer with more pores the inner extruder prints more material compared to the outer extruder.

Figure 9:
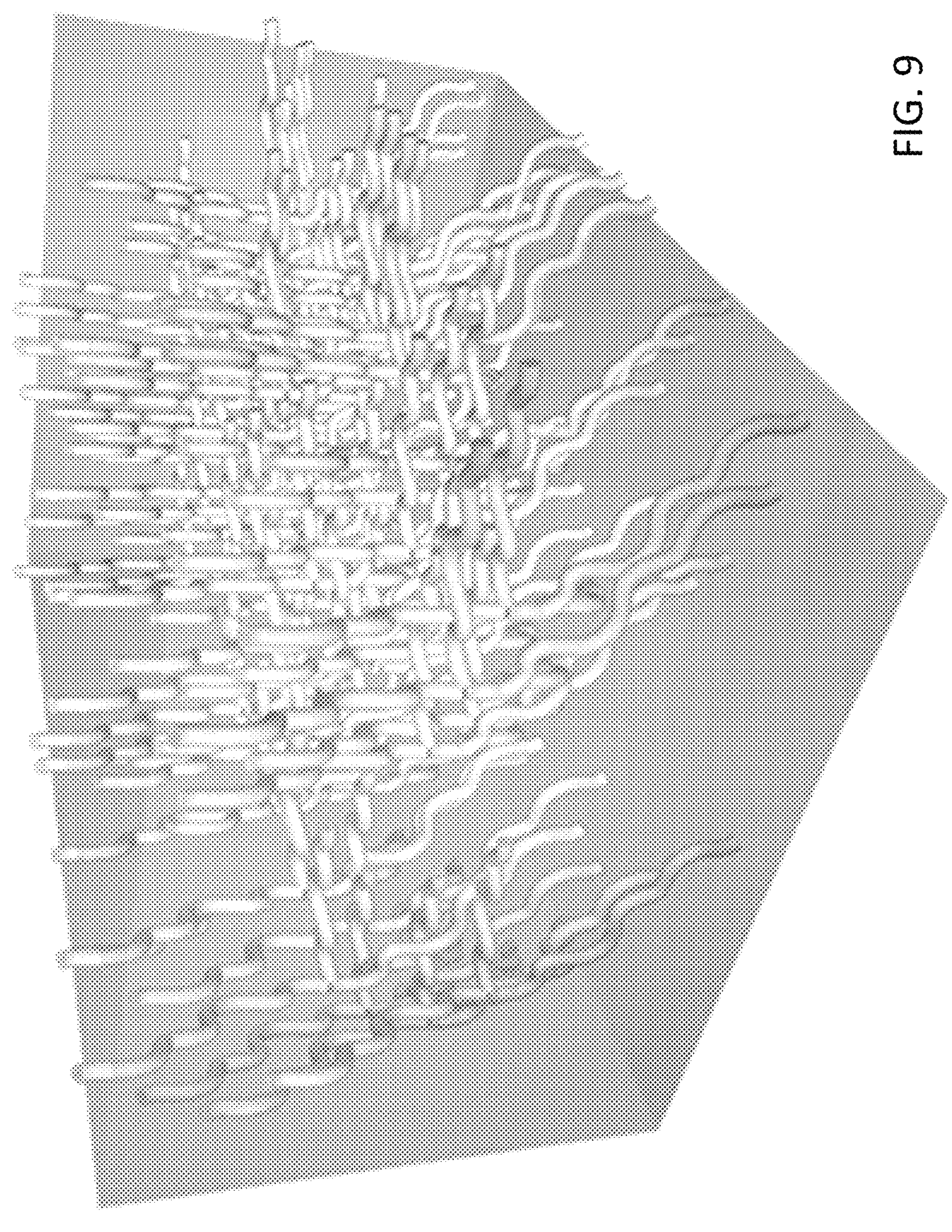
FIG. 9 shows schematically a 3D layout of the pores formed by the selective removing of the third medium from the 3D structure. The size, layout and structure of these pores can be customized and can vary in diameter between 0.1 nm to 5 mm.

By printing or depositing the third medium that is used as a sacrificial material, which can be selectively removed by exposure to liquid solvents (water, solvents or gases), it can controllably "print-out" the pores density, sizes, distribution, and architecture within the 3D structure of the scaffold, as shown in FIG. 9. These pores are formed after the third medium has been completely eliminated, leaving behind "empty voids". The diameter of the extruders also plays a very significant role in the formation of the resulting pore sizes. A small diameter inner extruder nozzle produces smaller pores in the scaffolds compared to the bigger diameter inner extruder nozzle. By placing the final scaffold in a selective solvent that specifically removed the third medium, it result in a 3D network of pores, with controllable and tunable characteristics.

FIG. 9 shows 3D arrangement of the pores formed by the selective removing of the third medium from the scaffold architecture. The size, arrangement and structure of these pores can be customized and can vary in diameter between 0.1 nm to 5 mm.

Also, the nozzles made from shape memory alloys can be used. The shape memory alloy nozzle is able to change its diameter as per the required nozzle diameter. If using regular steel nozzles, then they will have to be changed back and forth to differently sized nozzle diameters, this will make 3D bio-printing procedure more manual as compared to becoming automatic.

After printing one layer of bone scaffold, alternatively the first medium particles can be deposited in order to embed them inside the scaffold material. The addition of bone particles will allow the control of the porosity of the scaffold.

The first medium particles are deposited from a separate extruder nozzle, deposited by electrostatic powder reposition processes, shaking, fluidizing beds, liquid of dry deposition, etc. The first medium particles can be triboelectric charged and sprinkled on the 3-D printed scaffold layer for their uniform distribution or pre-designed deposition.

In addition, one or more of media 4-6 may also be incorporated in to the above disclosed fabricating processes and/or are directly deposited on the scaffolds obtained by the above disclosed fabricating processes, so that in addition to the first medium, the second medium and the pores, the scaffolds may also include the one or more of media 4-6. In some embodiments, an additional nozzle is used to spray continuously or when programed the solvent of the second medium, the third medium, the fourth medium, the fifth medium, etc. The solvent is sprayed by a fix or moving head and the flow rate is controlled from 0 to 10 liters/sec, and allows the first medium particles to get embedded in the second medium, the third medium, the fourth medium, the fifth medium, the sixth medium, etc. Mechanical pressure can be applied to adjust the level or embedment and shape the scaffold.

In some embodiments, the nozzle can be cylindrical, rectangle, square, star, or "slit" like to allow the materials to be deposited as atomized droplets, cylindrical paste or curtain-like.

In some embodiment, the sample stage on which 3D deposition of the scaffold takes place includes a back and forth moving support system (a platform). The sample stage moves back and forth under the nozzles and the first medium powder-like deposition system. The type of belt design allows building numerous layers of the scaffold by 3D deposition.

In some embodiments, the size of the scaffold is dependent upon the bone defect that needs to be regenerated and it can have the shapes of the bone defects. The scaffolds can have a variety of shapes: rectangular, cylindrical, spherical, tubular, non-uniform, or the shape of an anatomically correct bone structure as obtained from a 3D CAT scan.

In some embodiments, the final scaffold can be osteoconductive, osteoinductive and supports cellular proliferation.

In some embodiments, the scaffold can be exposed to plasma discharge treatment and can be used while electromagnetic excitation (laser, ultrasounds, RF, magnetic fields, etc.) is applied to the scaffold positioned in vivo into the bone volume that needs to be regenerated.

In some embodiments, the scaffold in one embodiment has a polymer film-like top surface, namely, a membrane with a thickness ranging from 0.1 nm to 5 mm and with variable pores ranging from 1 nm to 5 mm, preferably less than 20 micrometers to limit or control or completely stop any cellular proliferation into the scaffold from the top, while allowing other cells to interact with the scaffold, from the other sides (lateral and bottom). For example, the top surface limits or completely removes the potential for epithelial cells to move into the scaffold bulk, while allowing the bone cells to interact and proliferate inside and onto the scaffold. The scaffold can carry and deliver drugs, cells or growth factors/proteins. The membrane allows for the cells, drugs, or growth factors/proteins not to be removed from the scaffold towards the epithelia, and to stay localized into the scaffold and the adjacent bone structure. The membrane can be loaded with drugs and growth factors different than those used for the bone scaffold structure.

In some embodiments, the scaffold alone or along with one or multiple combinations of cells, drugs/antibiotics, growth factors/proteins can be placed into a bone defects of various shapes or sizes, or in bone defects that have 3, 2, or 1 bone walls/surfaces. In another embodiment, the scaffold alone or along with one or multiple combinations of cells, drugs/antibiotics, growth factors/proteins can be placed next to a bone wall in order to increase the amount of bone formed along that particular bone surface.

In some embodiments, the cells comprise, but are not limited to, epithelial cells, neurons, glial cells, astrocytes, podocytes, mammary epithelial cells, islet cells, endothelial cells, mesenchymal cells, muscle cells, striated muscle cells, fibroblasts, hepatocytes, ligament fibroblasts, tendon fibroblasts, chondrocytes, or a mixture thereof.

In some embodiments, the growth factors comprise, but are not limited to, platelet-rich plasma (PRP), platelet-derived growth factor (PDGF), vascular endothelial growth factor (VEGF), fibroblast growth factor (FGF), Dorsalin-1, GDF-1, GDF-3, GDF-8, GDF-9, GDF-12, GDF-14, IGF-I, IGF-II, TGF-p, TGF, BMP-Sb, BMP-2, BMP-3, BMP-4, BMP-5, BMP-6, BMP-7, BMP-8, BMP-9, BMP-10, BMP-11, BMP-12, BMP-13, BMP-14, BMP-15, deoxyribonucleic acid (DNA), ribonucleic acid (RNA), plasmids, proteins, or a mixture thereof, wherein BMP is bone morphogenetic protein, GDF is growth differentiation factor, IGF is insulin growth factor, and TGF is transforming growth factor.

In some embodiments, the drugs comprise, but are not limited to, doxorubicin, mitotane, cisplatin, carboplatin, etoposide, cyclophosphamide, vincristine, abitrexate, dactinomycin, doxorubicin hydrochloride, denosumab, ifosfamide, actinomycin, docetaxel, gemcitabine, irinotecan, temozolomide, topotecan, paclitaxel, granulocyte colony stimulating factor, 5-fluorouracil, antimicrobials, anti-inflammatory, or a mixture thereof.

In some embodiments, the scaffold can be used for dental applications, where the scaffold is placed into an extraction socket, around the tooth root, around the implant surface, large segmental bone defect, alone or in the presence of antibiotics, drugs, cells or growth factors.

In some embodiments, the scaffold can be used for the partial or complete craniomaxillofacial bone regeneration such as, but not limited to, regenerating bone gaps or the entire structure in the mandible, skull, nasal bone and septum, maxilla, zygomatico-maxillary structure, maxilla, etc.

In some embodiments, the scaffold can be used for the partial or complete regeneration of long bones such as, but not limited to, tibia, femur, humerus, ulma, radius, fibula, patella, phalanges, metatarsals, metacarpals, sacrum, pelvic structure, vertebrae, ribs, spinal column, cervical vertebrae, etc.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

REFERENCE LIST

[1]. Alghazali, K. M., Nima, Z. A., Hamzah, R. N., Dhar, M. S., Anderson, D. E. and Biris, A. S. 2015. Bone-tissue engineering: complex tunable structural and biological responses to injury, drug delivery, and cell-based therapies. Drug Metabolism Reviews, 47, 431-454.

[2]. Do, A.-V., Khorsand, B., Geary, S. M. and Salem, A. K. 2015. 3D Printing of Scaffolds for Tissue Regeneration Applications. Advanced healthcare materials, 4, 1742-1762.

[3]. IKADA, Y. 2006. Challenges in tissue engineering. Journal of the Royal Society Interface, 3, 589-601.

[4]. Keating, J. F. and Mcqueen, M. M. 2001. Substitutes for autologous bone graft in orthopaedic trauma. J Bone Joint Surg Br, 83, 3-8.

[5]. Pangarkar, N. and Hutmacher, D. W. 2003. Invention and business performance in the tissue-engineering industry. Tissue Eng, 9, 1313-1322.

[6]. Rousseau, M., Anderson, D. E., Lillich, J. D., Apley, M. D., Jensen, P. J. and Biris, A. S. 2014. In vivo assessment of a multicomponent and nanostructural polymeric matrix as a delivery system for antimicrobials and bone morphogenetic protein-2 in a unicortical tibial defect in goats. Am J Vet Res, 75, 240-250.

What is claimed is:

1. A biocompatible structure useable for tissue regeneration, comprising:

a scaffold obtained by treating a three-dimensional (3D) structure, the 3D structure comprising one or more base layered structures, wherein each base layered structure comprises at least a first layer and a second layer surrounded by the first layer, wherein the first layer and the second layer are formed of different materials, the first layer comprises a first composition comprising at least one of a first medium, a second medium and a third medium, and the second layer comprises a second composition comprising at least another of the first medium, the second medium and the third medium; wherein the first medium comprises bone particles, the second medium comprises a polymer that is dissolvable or removable in a first solvent, and the third medium comprises solid particulates that are dissolvable or removable in a second solvent different than the first solvent;

wherein each base layered structure is formed by co-extruding the first composition and the second composition from a multi-nozzle deposition system comprising an outer extruder nozzle and an inner extruder nozzle disposed concentrically or eccentrically inside the outer extruder nozzle, wherein the first layer is formed by the outer extruder nozzle and the second layer is formed by the inner extruder nozzle such that the second layer is entirely surrounded by the first layer in the cross-section of said base layered structure; and wherein the 3D structure is treated with the second solvent to dissolve the solid particulates of the third medium therefrom so as to remove the solid particulates from the 3D structure and form pores at positions of the solid particulates therein, thereby resulting in the scaffold having a porosity that is adjustable by sizes of the solid particulates and concentration of the solid particulates in the 3D structure.

2. The biocompatible structure of claim 1, wherein the first layer comprises the first medium and the second medium, and the second layer comprises the third medium; or wherein the first layer comprises the first medium and the third medium, and the second layer comprises the second medium; or wherein the first layer comprises the second medium and the third medium, and the second layer comprises the first medium; or wherein the first layer comprises the first medium, and the second layer comprises the second medium and the third medium; or wherein the first layer comprises the second medium, and the second layer comprises the first medium and the third medium.

3. The biocompatible structure of claim 1, wherein the first layer comprises the second medium, and the second layer comprises the third medium.

4. The biocompatible structure of claim 3, wherein each base layered structure further comprises a third layer comprising the first medium deposited on the first layer.

5. The biocompatible structure of claim 1, wherein the 3D structure comprises a plurality of base layered structures attached to each other horizontally and/or vertically.

6. The biocompatible structure of claim 5, wherein the scaffold contains no polymer columns horizontally and/or vertically.

7. The biocompatible structure of claim 1, wherein the first medium and the second medium are arranged in layers with the second medium arranged in horizontal or vertical geometries.

8. The biocompatible structure of claim 1, wherein the first medium and the second medium arranged in alternating layers with the second medium arranged in horizontal and vertical geometries and the first medium disposed to separate the second medium horizontally and vertically.

9. The biocompatible structure of claim 1, wherein the second medium is deposited in a pattern including a continuous u-shaped line that has a repeatable pattern having a first half circle, a first straight line connected to the first half circle and a second half circle opposed to the first half circle and a second straight line connected to the second half circle, two said continuous u-shaped lines being aligned orthogonally to each other, a plurality of irregular circular shapes, a plurality of horizontal lines and a plurality of vertical lines aligned to each other to form a plurality of square shapes, a first plurality of lines and a second plurality of lines aligned to each other to form a plurality of quadrilateral shapes, or a plurality of hexagonal shapes.

10. The biocompatible structure of claim 1, wherein the bone particles comprise human bone particles, animal bone particles, and/or artificial bone particles.

11. The biocompatible structure of claim 1, wherein the bone particles have sizes in a range between 1 nm to 100 mm.

12. The biocompatible structure of claim 1, wherein the polymer is a natural or synthetic biocompatible and/or biodegradable polymer.

13. The biocompatible structure of claim 1, wherein the solid particulates of the third medium are configured to remain structurally intact in the presence of the first medium and the second medium prior to treatment with the second solvent.

14. The biocompatible structure of claim 1, further comprising a fourth medium, and wherein the fourth medium is a polymer with a faster or longer bio-degradation time in a biological system compared to the second medium.

15. The biocompatible structure of claim 14, wherein each of the second medium, the third medium and the fourth medium has degradation rates ranging from 1 second to 100 months.

16. The biocompatible structure of claim 14, wherein the fourth medium is deposited in equal or variable ratios compared to the second medium.

17. The biocompatible structure of claim 1, wherein the porosity of the scaffold varies from 1 to 99%.

18. The biocompatible structure of claim 1, wherein the scaffold is loaded with a plurality of cells, a plurality of drugs, or a plurality of growth factors.

19. The biocompatible structure of claim 1, wherein the scaffold is designed to have a non-uniform density and packing density, wherein the density at edges of the scaffold is higher or lower compared to that in an interior of the scaffold.

* * * * *